United States Patent
DeLuca et al.

(10) Patent No.: US 7,541,349 B2
(45) Date of Patent: Jun. 2, 2009

(54) 2-METHYLENE-19-NOR-(23S)-25-DEHYDRO-1α-HYDROXYVITAMIN D₃-26,23-LACTONE AND 2-METHYLENE-19-NOR-(23R)-25-DEHYDRO-1α-HYDROXYVITAMIN D₃-26,23-LACTONE

(75) Inventors: Hector F. DeLuca, Deerfield, WI (US); Lori A. Plum, Arena, WI (US); Margaret Clagett-Dame, Deerfield, WI (US); Grazia Chiellini, Madison, WI (US); Pawel Grzywacz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/767,085

(22) Filed: Jun. 22, 2007

(65) Prior Publication Data

US 2007/0259953 A1   Nov. 8, 2007

Related U.S. Application Data

(63) Continuation of application No. 11/390,999, filed on Mar. 28, 2006, now Pat. No. 7,235,680.

(60) Provisional application No. 60/666,129, filed on Mar. 29, 2005.

(51) Int. Cl.
*A61K 31/59* (2006.01)
*C07C 401/00* (2006.01)

(52) U.S. Cl. ....................... 514/167; 552/653

(58) Field of Classification Search ................ 514/167; 552/653

See application file for complete search history.

(56) References Cited

U.S. PATENT DOCUMENTS

| | | | |
|---|---|---|---|
| 4,666,634 A | 5/1987 | Miyamoto et al. | |
| 5,086,191 A | 2/1992 | DeLuca et al. | |
| 5,536,713 A | 7/1996 | DeLuca et al. | |
| 5,585,369 A | 12/1996 | DeLuca et al. | |
| 5,843,928 A | 12/1998 | DeLuca et al. | |
| 5,936,105 A * | 8/1999 | Paaren | 552/653 |
| 5,945,410 A | 8/1999 | DeLuca et al. | |
| 6,127,559 A | 10/2000 | DeLuca et al. | |
| 6,384,087 B1 | 5/2002 | Zemel et al. | |
| 6,537,981 B2 | 3/2003 | DeLuca et al. | |
| 6,566,352 B1 | 5/2003 | DeLuca et al. | |
| 6,579,861 B2 | 6/2003 | DeLuca et al. | |
| 6,627,622 B2 | 9/2003 | DeLuca et al. | |
| 2002/0091109 A1 | 7/2002 | Takenouchi et al. | |
| 2002/0192264 A1 | 12/2002 | Zemel et al. | |
| 2004/0220418 A1 | 11/2004 | DeLuca et al. | |
| 2005/0004085 A1 | 1/2005 | DeLuca et al. | |
| 2005/0065088 A1 | 3/2005 | Thompson | |
| 2005/0065133 A1 | 3/2005 | Lee et al. | |
| 2005/0065180 A1 | 3/2005 | Lee | |
| 2005/0070512 A1 | 3/2005 | Lee | |

OTHER PUBLICATIONS

*The Vitamins—Chemistry, Physiology, Pathology*—vol. II (eds. W. H. Sebrell, Jr. and Robert S. Harris), Chapter 6, pp. 264-266; published by Academic Press Inc., New York, 1954.

C. H. Jacobus et al., "Hypervitaminosis D associated with drinking milk," *The New England Journal of Medicine*, vol. 326, No. 18, pp. 1173-1177, Apr. 30, 1992; Abstract printed from the Internet on Oct. 29, 2008 at http://content.nejm.org/cgi/content/abstract/326/18/1173?ijkey=770cd6c231b.

P. Koutkia et al, Vitamin D Intoxication Associated with an Over-the-Counter Supplement, *The New England Journal of Medicine*, vol. 345, No. 1, pp. 66-67, Jul. 5, 2001; printed from the Internet on Oct. 29, 2008 at http://content.nejm.org/cgi/content/full/345/1/66-a?ijkey=b88a3d7ae2a941a7b04797b24.

Baggiolini et al., "Stereocontrolled Total Synthesis of 1α,25-Dihydroxycholecalciferol and 1α,25-Dihydroxyergocalciferol," J. Org. Chem.,51, 3098 (1986); published by American Chemical Society.

Competitive VDR Binding $K_i$:  $1.25(OH)_2D_3 = 2.2 \times 10^{-11}$ M
GC-3 = $1.0 \times 10^{-9}$ M
HLV = $4.6 \times 10^{-9}$ M Bury, Y. et al.., "Structure Activity Relationship of Carboxylic Ester Antagonists of the Vitamin $D_3$ Receptor," Mol. Pharmacol., 58 (5), 1067 (2000); published by The American Society for Pharmacology and Experimental Therapeutics; published by American Chemical Society.

Daniewski et al., "A Novel Silylcopper Catalyst for the Reductive Bromination of Hajos Dione. Improved Preparation of a CD Synthon for the Synthesis of Vitamin D," J. Org. Chem., 66, 626-628 (2001); published by American Chemical Society.

Endres, et al., BioChemistry, 2000, 2123-2129.

Herdick, M. et al., "Carboxylic ester antagonists of $1\alpha,25$-dihydroxyvitamin $D_3$ show cell-specific actions," Chem. Biol., 7 (11), 885 (2000); published by Elsevier Science Ltd.

Herdick, M. et al., "Antagonistic Action of a 25-Carboxylic Ester Analogue of $1\alpha,25$-Dihydroxyvitamin $D_3$ Is Mediated by a Lack of Ligand-induced Vitamin D Receptor Interaction with Coactivators," J. Biol. Chem., 275 (22), 16506 (2000); published by The American Society for Pharmacology and Experimental Therapeutics.

Hiroshi, H. et al., Abstract of JP 03210156, Sep. 13, 1991.

Ishizuka, et al., BioChemistry, 1984, 23, 1473-1478.

Ishizuka, S. et al., "Vitamin D antagonist, TEI-9647, inhibits osteoclast formation induced by $1\alpha,25$-hydroxyvitamin $D_3$ from pagetic bone marrow cells," J. Steroid Biochem. Mol. Biol., 89-90 (1-5), 331 (2004); published by Elsevier Ltd.

Ishizuka, S. et al., "Antagonistic Actions in Vivo of (23S)-25-Dehydro-$1\alpha$-Hydroxyvitamin $D_3$-26,23-Lactone on Calcium Metabolism Induced by $1\alpha,25$-Dihydroxyvitamin $D_3$," Endocrinology, 142 (1), 59 (2001); published by The Endocrine Society.

Lythgoe, et al., "Calciferol and its Relatives. Part 22. A Direct Total Synthesis of Vitamin $D_2$ and Vitamin $D_3$," J. Chem. Soc. Perkin Trans. I, N6, 590 (1978).

Lythgoe, "Synthetic Approaches to Vitamin D and its Relatives," Chem. Soc. Rev., 9, 449 (1983).

Mascareñas et al., "Studies of the Synthesis of Side-Chain Hydroxylated Metabolites of Vitamin D. 3. Synthesis of 25-Ketovitamin $D_3$ and 25-Hydroxyvitamin $D_3$," J. Org. Chem., 51, 1269 (1986).

Mincione et al., "Improved Conversion of Vitamin $D_2$ into the Windaus Ketone and its Regioselective Hydroxylation via Organoboranes at $C_{26}$," Synth. Commun., 19, 723 (1989).

Miura, D. et al., "Antagonistic Action of Novel $1\alpha,25$-Dihydroxyvitamin $D_3$-26,23-lactone Analogs on Differentiation of Human Leukemia Cells (HL-60) Induced by $1\alpha,25$-Dihydroxyvitamin $D_3$," J. Biol. Chem., 274 (23), 16392 (1999); published by The American Society for Biochemistry and Molecular Biology, Inc.

Nishii et al., "The Development of Vitamin $D_3$ Analogues for the Treatment of Osteoporosis," Osteoporosis Int. Suppl. 1, 190 (1993); published by European Foundation for Osteoporosis.

Perlman, et al., "$1\alpha$, 25-Dihydroxy-19-Nor-Vitamin $D_3$, a Novel Vitamin D-related Compound with Potential Therapeutic Activity," Tetrahedron Lett. 31(13), 1823 (1990); published by Pergamon Press plc.

Perlman et al., "Novel Synthesis of 19-Nor-Vitamin D Compounds," Tetrahedron Lett., 32 (52), 7663 (1991);published by Pergamon Press plc.

Peterson et al., "Studies of the Ketone Obtained from the Ozonolysis of Vitamin D. Molecular Mechanics Calculations for It and Related Hydrindanones," J. Org. Chem., 51, 1948 (1986); published by American Chemical Society.

Posner et al., "Stereocontrolled Total Synthesis of Calcitriol Derivatives: 1,25-Dihydroxy-2-(4'-hydroxybutyl)vitamin $D_3$ Analogs of an Osteoporosis Drug," J. Org. Chem., 59, 7855 (1994); published by American Chemical Society.

Posner et al., "2-Fluoroalkyl A-Ring Analogs of 1,25-Dihydroxyvitamin $D_3$-Stereocontrolled Total Synthesis via Intramolecular and Intermolecular Diels-Alder Cycloadditions. Preliminary Biological Testing," J. Org. Chem., 60, 4617 (1995).

Saito et al., "Remarkable effect of $2\alpha$-modification on the VDR antagonistic activity of $1\alpha$-hydroxyvitamin $D_3$-26,23-lactones," Org. Biomol. Chem., 1, 4396 (2003); published by The Royal Society of Chemistry.

Sardina et al., "Studies on the Synthesis of Side-Chain Hydroxylated Metabolites of Vitamin D. 2. Stereocontrolled Synthesis of 25-Hydroxyvitamin $D_2$," J. Org. Chem., 51, 1264 (1986); published by American Chemical Society.

Sicinski, R. R. et al., "New $1\alpha,25$-Dihydroxy-19-norvitamin $D_3$ Compounds of High Biological Activity: Synthesis and Biological Evaluation of 2-Hydroxymethyl, 2-Methyl, and 2-Methylene Analogues," J. Med. Chem., 41, 4662-4674 (1998); published by American Chemical Society.

Toell, A. et al., "Different Molecular Mechanisms of Vitamin $D_3$ Receptor Antagonists," Mol. Pharmacol., 59 (6), 1478 (2001); published by The American Society for Pharmacology and Experimental Therapeutics.

Toh et al., "Studies on a Convergent Route to Side-Chain Analogues of Vitamin D: 25-Hydroxy-23-oxavitamin $D_3$," J. Org. Chem., 48, 1414 (1983); published by American Chemical Society.

Väisänen, S. et al., "Critical Role of Helix 12 of the Vitamin $D_3$ Receptor for the Partial Agonism of Carboxylic Ester Antagonists," J. Mol. Biol., 315 (2), 229 (2002); published by Academic Press.

* cited by examiner

*Primary Examiner*—Sabiha N. Qazi
(74) *Attorney, Agent, or Firm*—Foley & Lardner LLP

(57) ABSTRACT

Compounds of formula 1A and 1B are provided where $X^1$ and $X^2$ are independently selected from H or hydroxy protecting groups. Such compounds may be used in preparing pharmaceutical compositions and are useful in treating a variety of biological disorders.

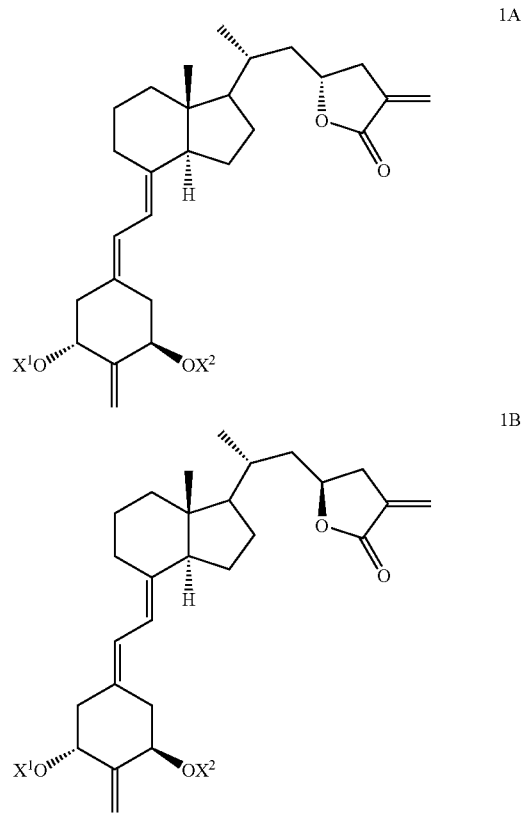

14 Claims, 7 Drawing Sheets

2-METHYLENE-19-NOR-(23S)-25-DEHYDRO-1α-HYDROXYVITAMIN D₃-26,23-LACTONE AND 2-METHYLENE-19-NOR-(23R)-25-DEHYDRO-1α-HYDROXYVITAMIN D₃-26,23-LACTONE

CROSS-REFERENCES TO RELATED APPLICATIONS

This application is a continuation of prior application Ser. No. 11/390,999, filed Mar. 28, 2006, which claimed the benefit of U.S. Provisional Application No. 60/666,129, filed Mar. 29, 2005.

FIELD OF THE INVENTION

This invention relates to vitamin D compounds, and more particularly to 2-methylene-19-nor-(23R)-25-dehydro-1α-hydroxyvitamin D₃-26,23-lactone ("GC-3") and 2-methylene-19-nor-(23S)-25-dehydro-1a-hydroxyvitamin D₃-26,23-lactone ("HLV"), and to pharmaceutical formulations that include these compounds or mixtures thereof. The invention also relates to the use of GC-3, HLV, salts thereof, and mixtures thereof in the preparation of medicaments for use in treating various diseases.

BACKGROUND OF THE INVENTION

The natural hormone, 1a,25-dihydroxyvitamin D₃ (also referred to as 1a,25-dihydroxycholecalciferol and calcitriol) and its analog in the ergosterol series, i.e. 1a,25-dihydroxyvitamin D₂ are known to be highly potent regulators of calcium homeostasis in animals and humans, and their activity in cellular differentiation has also been established, Ostrem et al., *Proc. Natl. Acad. Sci. USA*, 84, 2610 (1987). Many structural analogs of these metabolites have been prepared and tested, including 1a-hydroxyvitamin D₃, 1a-hydroxyvitamin D₂, various side chain homologated vitamins, and fluorinated analogs. Some of these compounds exhibit an interesting separation of activities in cell differentiation and calcium regulation. This difference in activity may be useful in the treatment of a variety of diseases as renal osteodystrophy, vitamin D-resistant rickets, osteoporosis, psoriasis, and certain malignancies. The structure of 1a,25-dihydroxyvitamin D₃ and the numbering system used to denote the carbon atoms in this compound are shown below.

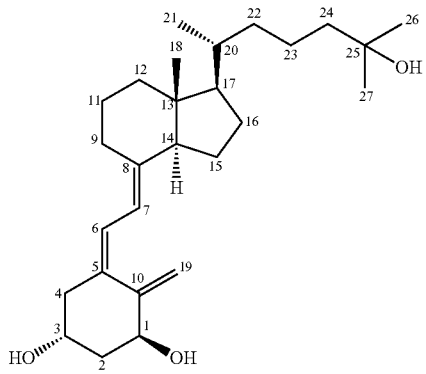

1α,25-Dihydroxyvitamin D₃ = 1α,25-Dihydroxycholecalciferol = Calcitriol

Another class of vitamin D analogs, i.e. the so called 19-nor-vitamin D compounds, is characterized by the replacement of the A-ring exocyclic methylene group (carbon 19), typical of the vitamin D system, by two hydrogen atoms. Biological testing of such 19-nor-analogs (e.g., 1a,25-dihydroxy-19-nor-vitamin D₃) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., *Tetrahedron Lett.* 31, 1823 (1990); Perlman et al., *Tetrahedron Lett.* 32, 7663 (1991), and DeLuca et al., U.S. Pat. No. 5,086,191).

In U.S. Pat. No. 4,666,634, 2β-hydroxy and alkoxy (e.g., ED-71) analogs of 1a,25-dihydroxyvitamin D₃ have been described and examined by the Chugai group as potential drugs for osteoporosis and as antitumor agents. See also Okano et al., *Biochem. Biophys. Res. Commun.* 163, 1444 (1989). Other 2-substituted (with hydroxyalkyl, e.g., ED-120, and fluoroalkyl groups) A-ring analogs of 1a,25-dihydroxyvitamin D₃ have also been prepared and tested (Miyamoto et al., *Chem. Pharm. Bull.* 41, 1111 (1993); Nishii et al., *Osteoporosis Int. Suppl.* 1, 190 (1993); Posner et al., *J. Org. Chem.* 59, 7855 (1994), and *J. Org. Chem.* 60, 4617 (1995)).

Various 2-substituted analogs of 1a,25-dihydroxy-19-nor-vitamin D₃ have also been synthesized, i.e. compounds substituted at the 2-position with hydroxy or alkoxy groups (DeLuca et al., U.S. Pat. No. 5,536,713), with 2-alkyl groups (DeLuca et al., U.S. Pat. No. 5,945,410), and with 2-alkylidene groups (DeLuca et al., U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs which are characterized by the presence of a methylene substituent at carbon 2 (C-2), a hydroxyl group at carbon 1 (C-1), and a shortened side chain attached to carbon 20 (C-20) have also been synthesized and tested. 1a-Hydroxy-2-methylene-19-nor-pregnacalciferol is described in U.S. Pat. No. 6,566,352 while 1a-hydroxy-2-methylene-19-nor-(20S)-homopregnacalciferol is described in U.S. Pat. No. 6,579,861 and 1a-hydroxy-2-methylene-19-nor-bishomopregnacalciferol is described in U.S. Pat. No. 6,627,622. All three of these compounds have relatively high binding activity to the vitamin D receptor and relatively high cell differentiation activity, but little if any calcemic activity as compared to 1a,25-dihydroxyvitamin D₃. Their biological activities make these compounds excellent candidates for a variety of pharmaceutical uses, as set forth in the '352, '861 and '622 patents.

SUMMARY OF THE INVENTION

The invention provides 2-methylene-19-nor-(23R)-25-dehydro-1a-hydroxyvitamin D₃-26,23-lactone ("GC-3"), 2-methylene-19-nor-(23S)-25-dehydro-1a-hydroxyvitamin D₃-26,23-lactone ("HLV"), and related compounds, pharmaceutical formulations that include GC-3 and/or HLV, and the use of these compounds or mixtures thereof in the preparation of medicaments for use in treating various disease states.

Therefore, in one aspect, the invention provides a vitamin D analog that includes a lactone functional group. In some such embodiments, the lactone includes an exocyclic methylene group. In some such embodiments, the exocyclic methylene group is bonded to the carbon atom adjacent to the carbonyl moiety of the lactone functional group. In some embodiments, the vitamin D analog is a 19-nor vitamin D analog.

Therefore, in one aspect, the invention provides compounds having the formula 1A, formula 1B, or a mixture thereof as shown below:

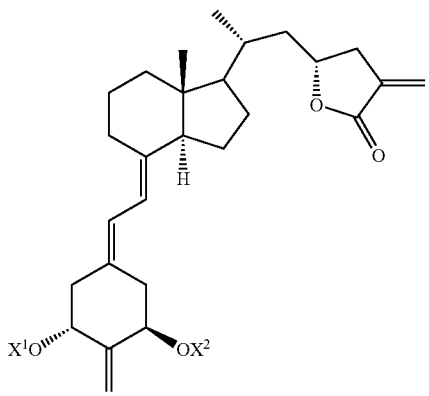

1A

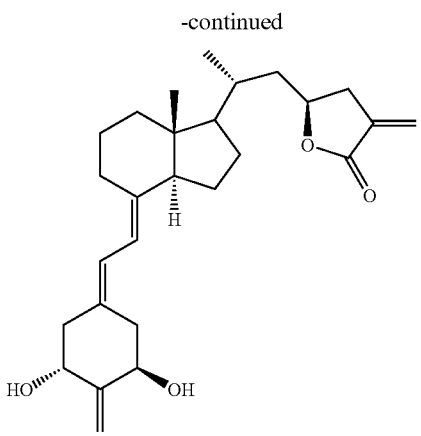

1B1

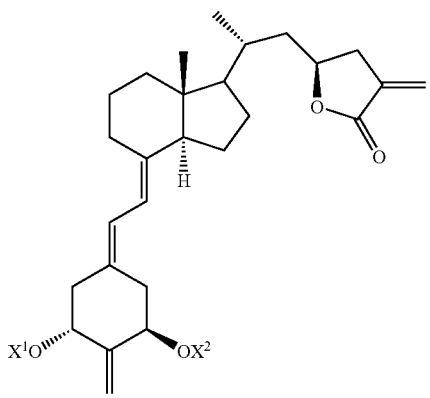

1B

In some such embodiments, the compounds of formulas 1A1 and 1B1 are compounds of formulas 1A2 and 1B2, or mixtures thereof, and have the structures shown below:

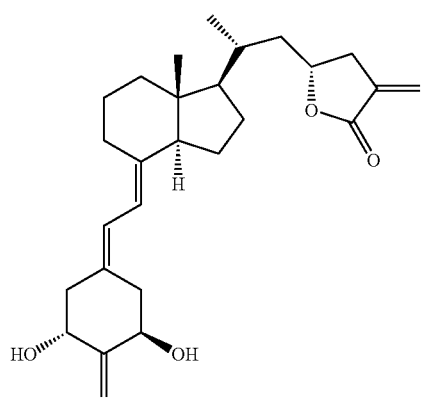

1A2 where $X^1$ and $X^2$ may be the same or different and are independently selected from H or hydroxy-protecting groups. In some embodiments, $X^1$ and $X^2$ are both hydroxy protecting groups such as silyl groups. In some such embodiments, $X^1$ and $X^2$ are both t-butyldimethylsilyl groups. In other embodiments, $X^1$ and $X^2$ are both H such that the compound shown as formula 1A above is 2-methylene-19-nor-(23R)-25-dehydro-1α-hydroxyvitamin $D_3$-26,23-lactone and the compound shown as formula 1B is 2-methylene-19-nor-(23S)-25-dehydro-1α-hydroxyvitamin $D_3$-26,23-lactone, or mixtures thereof, having the isomeric formulas 1A1 and 1B1 as shown below:

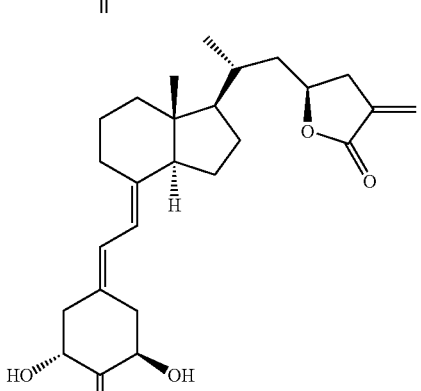

1B2

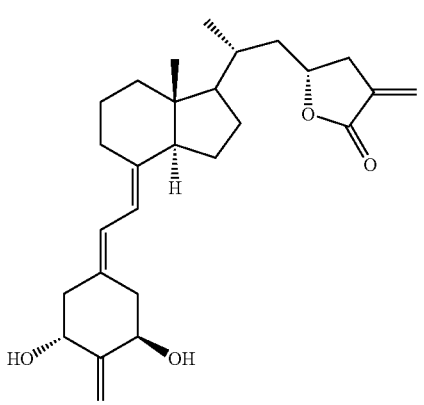

1A1

In some such embodiments, the compounds may be present in a purified form. In other embodiments, the compounds in a composition may be present as a mixture. In some embodiments, the mixture includes the compound of formula 1A and the compound of formula 1B, and the ratio of the compound of formula 1A to the compound of formula 1B ranges from 50:50 to 99.9:0.1. In some such embodiments, the ratio of the compound of formula 1A to the compound of formula 1B ranges from 70:30 to 99.9:0.1, from 80:20 to 99.9:0.1, from 90:10 to 99.9:0.1, or from 95:5 to 99.9:0.1. In other embodiments, the mixture includes the compound of formula 1A and the compound of formula 1B, and the ratio of the compound of formula 1B to the compound of formula 1A ranges from 50:50 to 99.9:0.1. In some such embodiments, the ratio of the compound of formula 1B to the compound of formula 1A ranges from 70:30 to 99.9:0.1, from 80:20 to 99.9:0.1, from 90:10 to 99.9:0.1, or from 95:5 to 99.9:0.1.

The above compounds exhibit desired, and highly advantageous, patterns of biological activity. Both GC-3 and HLV bind to the vitamin D receptor, but both of these compounds are less active in this respect than is 1a,25-dihydroxyvitamin $D_3$. Both GC-3 and HLV also show less activity than 1,25-$(OH)_2D_3$ in inducing differentiation of HL-60 cells. However, GC-3 and HLV have the ability to antagonize 1α,25-dihydroxyvitamin $D_3$-mediated transcription. GC-3 and HLV have no calcemic activity when measured by bone calcium mobilization, but do retain the ability to elevate intestinal calcium transport. Because these compounds act as antagonists in vitro and weak agonists in vivo, these compounds could serve as useful therapeutic agents when administered locally to some tissues. These compounds may thus find use in therapies for treating asthma, hypercalcemia, eczema, sarcoidosis, and vitamin D intoxication. These compounds are characterized by relatively high binding to the vitamin D receptor compared to 1a,25-dihydroxyvitamin $D_3$, while also retaining the ability to elevate intestinal calcium transport. However, these compounds appear to have no calcemic activity as compared to 1a,25-dihydroxyvitamin $D_3$ in their ability to mobilize calcium from bone. These compounds also show antagonistic activity when administered along with 1a,25-dihydroxyvitamin $D_3$. Thus, these compounds may be useful in therapies for treating asthma, hypercalcemia, eczema, sarcoidosis, and vitamin D intoxication.

The compounds described herein are also characterized by moderate cell differentiation activity. Thus, these compounds may also be used as therapeutic agents for the treatment of psoriasis and/or an anti-cancer agents, especially against leukemia, colon cancer, breast cancer and prostate cancer. In addition, due to their moderate cell differentiation activities, the compounds may be used as therapeutic agents for the treatment of various skin conditions including wrinkles, lack of adequate dermal hydration, i.e. dry skin, lack of adequate skin firmness, i.e. slack skin, and insufficient sebum secretion. Use of the compounds thus moisturizes skin and improves the barrier function of skin.

In another aspect, the invention provides a method of antagonizing the vitamin D receptor. The method includes administering a compound or pharmaceutical composition of the invention to an animal subject. The compound administered to the subject antagonizes the vitamin D receptor.

In another aspect, the invention provides a method of treating asthma or eczema in an animal subject suffering from asthma or eczema. The method includes administering an effective amount of a compound or a pharmaceutical composition of the invention to the animal subject. Administration of the compound leads to a reduction in the symptoms associated with asthma or eczema.

In some embodiments of the methods of the invention, the compound or pharmaceutical composition is administered orally, rectally, parenterally, transdermally, or topically. In other embodiments, the compound or pharmaceutical formulations is administered in an aerosol which may be accomplished using an inhaler or a nebulizer.

In another aspect, the invention provides the use of a compound of the invention in the preparation of a pharmaceutical composition or medicament for antagonizing the vitamin D receptor and/or for treating asthma or eczema in an animal subject suffering from asthma or eczema. In some embodiments, the compounds are used to prepare an aerosol which may include a glycol compound such as propylene glycol.

The compounds of the invention may be used to prepare pharmaceutical formulations or medicaments that include a compound or a mixture of the compounds of the invention in combination with a pharmaceutically acceptable carrier. Such pharmaceutical formulations and medicaments may be used to treat various biological disorders such as those described herein, including those mediated by a vitamin D receptor. Methods for treating such disorders typically include administering an effective amount of the compound, or an appropriate amount of a pharmaceutical formulation or a medicament that includes the compound, to a subject suffering from the biological disorder. In some embodiments, the subject is a mammal. In some such embodiments, the mammal is selected from a rodent, a primate, a bovine, an equine, a canine, a feline, an ursine, a porcine, a rabbit, or a guinea pig. In some such embodiments, the mammal is a rat or is a mouse. In some embodiments, the subject is a primate such as, in some embodiments, a human.

The compounds may be present in a composition to treat the above-noted diseases and disorders in an amount from about 0.01 μg/gm to about 1 mg/gm of the composition, preferably from about 0.1 μg/gm to about 500 μg/gm of the composition, and may be administered topically, transdermally, orally, rectally, or parenterally in dosages of from about 0.01 μg/day to about 1 mg/day, preferably from about 0.1 μg/day to about 500 μg/day.

Further objects, features and advantages of the invention will be apparent from the following detailed description and drawings.

BRIEF DESCRIPTION OF THE DRAWINGS

FIG. 1 is a graph comparing the relative activity of GC-3, HLV, and 1,25$(OH)_2D_3$ to compete for binding with [$^3$H]-1, 25-$(OH)_2$-$D_3$ to the full-length recombinant rat vitamin D receptor.

FIG. 2 is a graph comparing the percent HL-60 cell differentiation as a function of concentration of GC-3, HLV, and 1,25$(OH)_2D_3$.

FIG. 3 is a graph comparing the in vitro transcription activity of 1,25$(OH)_2D_3$ alone with that of 1,25$(OH)_2D_3$ in combination with GC-3.

FIG. 4 is a graph comparing the in vitro transcription activity of 1,25$(OH)_2D_3$ alone with that of 1,25$(OH)_2D_3$ in combination with HLV.

FIG. 5 is a graph comparing the in vitro transcription activity of HLV, GC-3, and 1,25$(OH)_2D_3$.

FIG. 6 is a bar graph comparing the bone calcium mobilization activity of GC-3, HLV, and 1,25$(OH)_2D_3$.

FIG. 7 is a bar graph comparing the intestinal calcium transport activity of GC-3, HLV, and 1,25$(OH)_2D_3$.

DETAILED DESCRIPTION OF THE INVENTION

Figure 1:
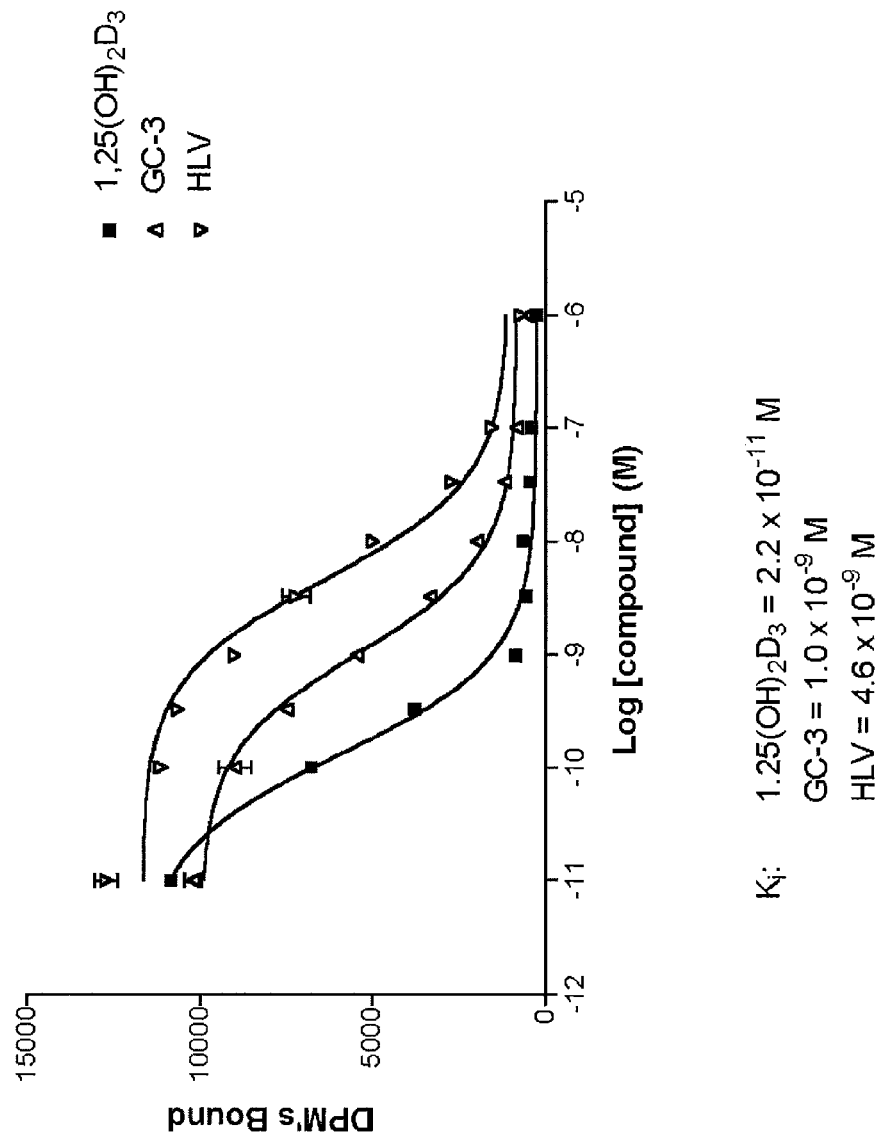
FIGS. 1-7 illustrate various biological activities of 2-methylene-19-nor-(23R)-1a,25-dihydroxyvitamin $D_2$ (referred to as "GC-3" in the Figures) and 2-methylene-19-nor-(23S)-1a,25-dihydroxyvitamin $D_2$ (referred to as "HLV" in the Figures) compared with those of the native hormone 1a,25-dihydroxyvitamin $D_3$ (referred to as "1,25$(OH)_2D_3$" in the Figures).

2-Methylene-19-nor-(23R)-25-dehydro-1a-hydroxyvitamin $D_3$-26,23-lactone ("GC-3") and 2-methylene-19-nor-(23S)-25-dehydro-1a-hydroxyvitamin $D_3$-26,23-lactone ("HLV") were synthesized, and tested, and found to be useful in treating a variety of biological disorders as described herein. Structurally, GC-3 has the formula 1A1 and HLV has the formula 1B1, as shown below:

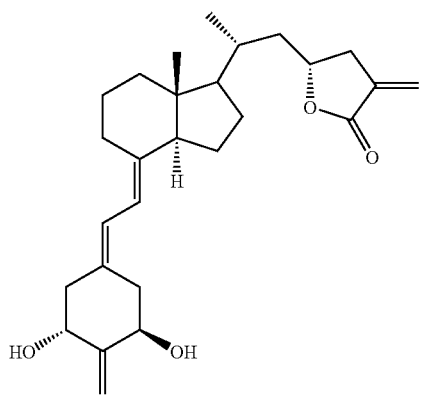

1A1

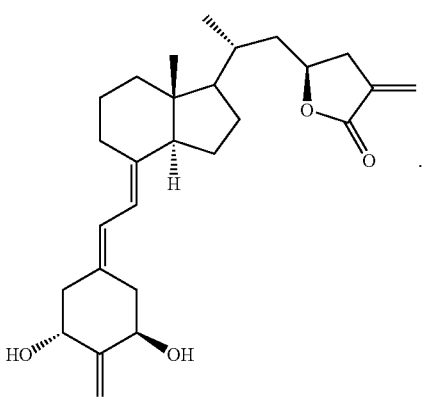

1B1

One step in the reaction sequence used in the preparation of the GC-3 and HLV isomers can be accomplished by condensing an appropriate bicyclic Windaus-Grundmann type ketone (II) with the allylic phosphine oxide III followed by TES removal, side chain elongation, lactone ring formation, and deprotection (removal of the $Y_1$ and $Y_2$ groups), in a later step.

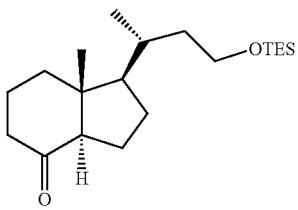

II

-continued

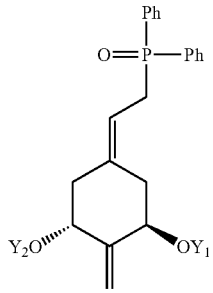

III

In phosphine oxide III, $Y_1$ and $Y_2$ are preferably hydroxy-protecting groups such as silyl protecting groups. The t-butyldimethylsilyl (TBDMS) group is an example of a particularly useful hydroxy-protecting group. The process described above represents an application of the convergent synthesis concept, which has been applied effectively to the preparation of numerous vitamin D compounds (see Lythgoe et al., *J. Chem. Soc. Perkin Trans. 1,* 590 (1978); Lythgoe, *Chem. Soc. Rev.* 9, 449 (1983); Toh et al., *J. Org. Chem.* 48, 1414 (1983); Baggiolini et al., *J. Org. Chem.* 51, 3098 (1986); Sardina et al., *J. Org. Chem.* 51, 1264 (1986); *J. Org. Chem.* 51, 1269 (1986); DeLuca et al., U.S. Pat. No. 5,086,191; DeLuca et al., U.S. Pat. No. 5,536,713; and DeLuca et al., U.S. Pat. No. 5,843,928 all of which are hereby incorporated by reference in their entirety and for all purposes as if fully set forth herein).

Phosphine oxide III is a convenient reagent that can be used to prepare a large number of 19-nor vitamin D compounds and may be prepared according to the procedures described by Sicinski et al., *J. Med. Chem.,* 41, 4662 (1998), DeLuca et al., U.S. Pat. No. 5,843,928; Perlman et al., *Tetrahedron Lett.* 32, 7663 (1991); and DeLuca et al., U.S. Pat. No. 5,086,191. Scheme I shows the general procedure for synthesizing phosphine oxide III as outlined in U.S. Pat. No. 5,843,928 which is hereby incorporated by reference in its entirety as if fully set forth herein. Modification of the method shown in Scheme I may be used to produce a large number of vitamin D analogs as will be apparent to those skilled in the art. For example, a wide variety of phosphonium compounds may be used in place of the $MePh_3P^+$ $Br^-$ used to convert ketone B to alkene C. Examples of such compounds include $EtPh_3P^+$ $Br^-$, $PrPh_3P^+$ $Br^-$, and compounds generally prepared by reaction of triphenylphosphine with an alkyl halide, an alkenyl halide, a protected-hydroxyalkyl halide, and a protected hydroxyalkenyl halide. Alkenes prepared using this procedure may then be carried through to prepare a phosphine oxide in an analogous manner to that used to prepare phosphine oxide H in Scheme I. Alternatively, an alkene analogous to compound C of Scheme I may be reduced with $(Ph_3P)_3RhCl$ and $H_2$ to provide other vitamin D analogs. See U.S. Pat. No. 5,945,410 and Sicinski, R. R. et al., *J. Med. Chem.,* 41, 4662-4674 (1998) both of which are hereby incorporated by reference in their entireties and for all purposes. Therefore, the procedure for forming the phosphine oxide shown in Scheme I may be used to prepare a wide variety of vitamin D analogs in addition to the compound of the present invention.

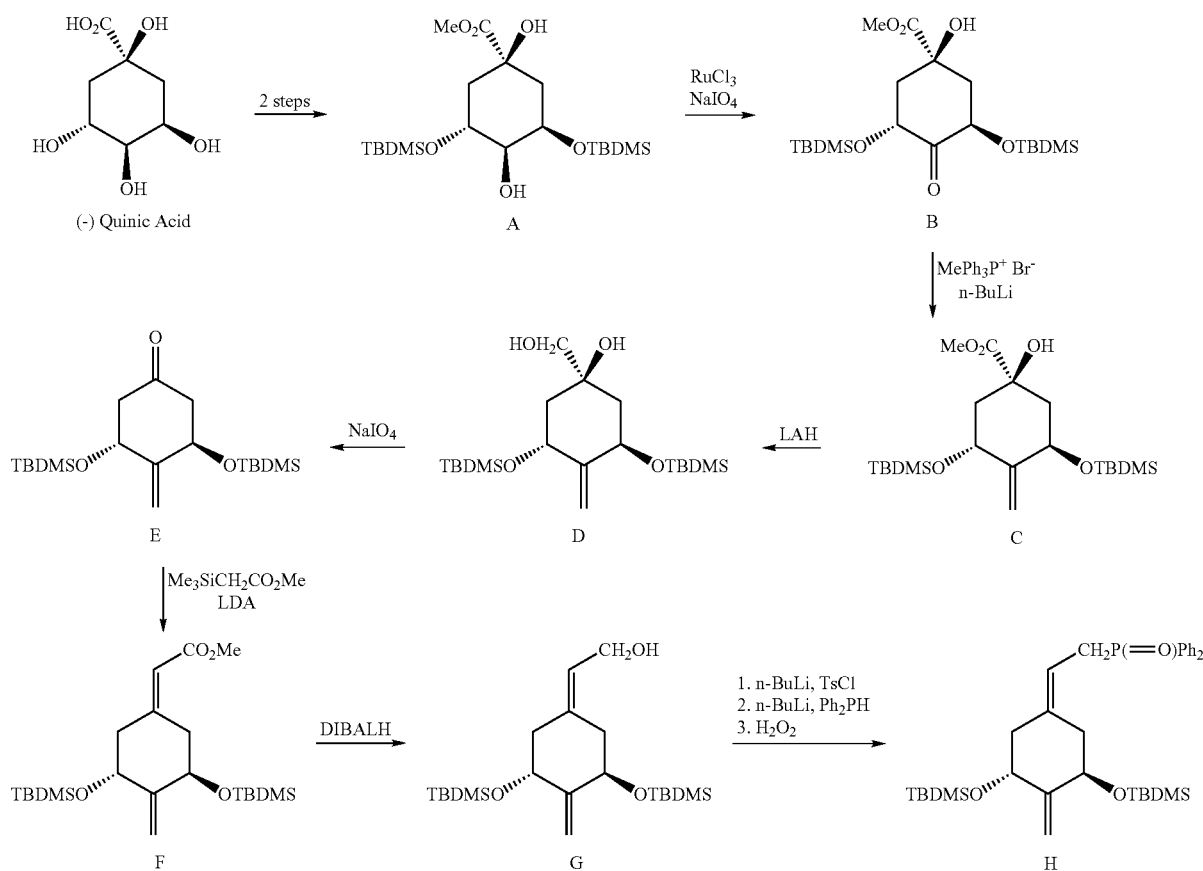

Scheme I

Hydroindanones of structure II can prepared by known methods or adapted methods as will be readily apparent to one of skill in the art and described herein. Specific examples of some important bicyclic ketones used to synthesize vitamin D analogs are those described in Mincione et al., *Synth. Commun.* 19, 723, (1989); and Peterson et al., *J. Org. Chem.* 51, 1948, (1986).

An overall process for synthesizing 2-alkylidene-19-nor-vitamin D compounds is illustrated and described in U.S. Pat. No. 5,843,928 which is hereby incorporated by reference in its entirety and for all purposes as if fully set forth herein.

As used herein, the term "hydroxy-protecting group" signifies any group commonly used for the temporary protection of the hydroxy (—OH) functional group, such as, but not limited to, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groups such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. Alkoxyalkyl protecting groups are groups such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group. An extensive list of protecting groups for the hydroxy functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for all purposes as if fully set forth herein.

A "protected hydroxy" group is a hydroxy group derivatized or protected by any of the above groups commonly used for the temporary or permanent protection of hydroxy functional groups, e.g., the silyl, alkoxyalkyl, acyl or alkoxycarbonyl groups, as previously defined.

EXAMPLES

Synthesis of 2-methylene-19-nor-(23R)-25-dehydro-1α-hydroxyvitamin $D_3$-26,23-lactone (GC-3) and 2-methylene-19-nor-(23S)-25-dehydro-1α-hydroxyvitamin $D_3$-26,23-lactone (HLV)

The synthesis and characteristics of various 19-nor vitamin D analogs is described in numerous United States patents including U.S. Pat. Nos. 5,843,928, 6,627,622, 6,579,861, 5,086,191, 5,585,369, and 6,537,981. Each of the above-described references is hereby incorporated by reference in its entirety and for all purposes as if fully set forth herein.

Schemes I, IIA, IIB, and IIC outline the synthetic procedures described below, in detail.

(8S,20S)-de-A,B-8-hydroxy-20-(hydroxymethyl)-pregnane (1)

A flame-dried 1000 mL three-necked flask was charged sequentially with 5.0 g (12.7 mmol) of ergocalciferol (commercially available from Sigma-Aldrich), 400 mL of anhydrous MeOH, and 5 mL (62 mmol) of anhydrous pyridine. The solution was cooled at $-78°$ C. and treated with $O_3$ until a deep blue color developed and persisted (approximately 20-30 minutes). The solution was subsequently flushed with $O_2$ for 15 minutes until the blue color faded. Solid sodium borohydride (4.5 g, 118.9 mmol) was added in portions over a 4 hour time period. The first portion of sodium borohydride was added at $-78°$ C., after 20 minutes a second portion of sodium borohydride was added. The reaction mixture was warmed to room temperature over a period of 3-4 hours, then the last portion of sodium borohydride was added. After being stirred for 18 hours at room temperature, the mixture was quenched with water, concentrated in vacuo and extracted with EtOAc. The combined organic phases were washed with 1 N HCl, saturated $NaHCO_3$, brine, dried over $MgSO_4$, filtered, and concentrated in vacuo. Purification by silica gel chromatography (15% EtOAc/hexanes) afforded 1.41 g (6.64 mmol) of diol in 52% yield as a white solid; $^1H$ NMR ($CDCl_3$, 600 MHz) δ 4.09 (dm, J=3.0 Hz, 1H), 3.64 (dd, J=10.5, 3.0 Hz, 1H), 3.38 (dd, J=10.5, 6.6 Hz, 1H) 1.99 (dm, J=13.2 Hz, 1H), 1.03 (d, J=7.2 Hz, 3H), 0.96 (s, 3H); $^{13}C$ NMR ($CDCl_3$) δ 69.26, 67.87, 52.97, 52.40, 41.89, 40.26, 38.27, 33.60, 26.69, 22.60, 17.43, 16.65, 13.61; exact mass calculated for $C_{13}H_{24}O_2$ $[M]^+$ 212.1776, found 212.1779.

(8S,20R)-de-A, B-8-hydroxy-20-(formylmethyl)-pregnane (3)

A solution of diol 1 (500 mg, 2.35 mmol) in 5 mL of anhydrous pyridine was cooled to $-25°$ C. A precooled solution of tosyl chloride (553 mg, 2.9 mmol) in 1 mL of anhydrous pyridine was added dropwise to the diol solution via cannula. Upon stirring for 3.5 hours at $-25°$ C., the reaction was warmed up to $0°$ C. and allowed to stir for an additional 20 hours. The mixture was extracted with $CH_2Cl_2$, washed with saturated $CUSO_4$ aqueous solution, dried over $MgSO_4$, filtered, and concentrated to give a residue which was chromatographed on a silica gel column (20% EtOAc/hexanes) to afford 600 mg (1.64 mmol) of the corresponding tosylate 2 in 70% yield. To a solution of 2 (300 mg, 0.82 mmol) in DMSO (2 mL) was added KCN (106 mg, 1.64 mmol), and the mixture was stirred at $70°$ C. for 1.5 hours. The mixture was diluted with $Et_2O$ and the organic layer washed with $H_2O$ and saturated NaCl aqueous solution, dried over $MgSO_4$ and concentrated. The residue was dissolved in $CH_2Cl_2$ (3 mL). To the solution was added a solution of DIBALH in toluene (0.9 mL, 0.902 mmol) at $0°$ C., and the mixture was stirred at the same temperature for 1.5 hours. To the mixture was added, 10% potassium sodium tartrate aqueous solution, and the aqueous layer was extracted with $Et_2O$. The organic layer washed with saturated aqueous NaCl solution, dried over $MgSO_4$ and concentrated. The residue was purified by flash column chromatography on silica gel (3% EtOAc/hexanes) to give 3 (133 mg, 0.59 mmol in 2 steps, 72%): $[α]^{20}_D$+18.8° (c 1.21, $CHCl_3$); $^1H$ NMR ($CDCl_3$, 400 MHz) δ 9.75 (d, J=2.4 Hz, 1H), 4.08 (s, 1H), 2.45 (dm, J=15.7 Hz, 1H), 2.15 (m, 1H), 1.00 (d, J=6.6 Hz, 3H), 0.98 (s, 3H); $^{13}C$ NMR ($CDCl_3$, 400 MHz) δ 69.17, 56.34, 52.54, 50.68, 41.99, 40.22, 33.54, 31.22, 27.40, 22.44, 19.85, 17.34, 13.50; exact mass calculated for $C_{14}H_{24}O_2$ $[M]^+$ 224.1776, found 224.1771.

(8S,20R)-de-A, B-8-hydroxy-20-(2-hydroxyethyl)-pregnane (4)

To a solution of 3 (100 mg, 0.443 mmol) in anhydrous EtOH (10 mL) was added $NaBH_4$ (85 mg, 2.22 mmol) at $0°$ C., and the mixture was stirred at the same temperature for 1.5 hours. The mixture was diluted with EtOAc, washed with water, 1 N HCl, saturated aqueous $NaHCO_3$ solution, brine, dried over $MgSO_4$, and concentrated. The residue was purified by flash column chromatography on silica gel (10% EtOAc/hexanes) to give the desired diol 4 (75 mg, 0.337 mmol, 76%) $^1H$ NMR ($CDCl_3$, 800 MHz) δ 4.06 (d, J=2.4 Hz, 1H), 3.69 (ddd, J=10.4, 8.8, 4.8 Hz 1H), 3.62 (ddd, J=10.4, 7.2, 7.2 Hz, 1H) 1.98 (dm, J=12.8 Hz, 1H), 0.92 (d, J=6.6 Hz, 3H), 0.91 (s, 3H) $^{13}C$ NMR ($CDCl_3$) δ 69.55, 61.05, 57.11, 52.82, 42.16, 40.61, 39.00, 33.78, 32.67, 27.49, 22.73, 18.93, 17.64, 13.70; exact mass calculated for $C_{14}H_{26}O_2$ $[M]^+$ 226.1933, found 226.1945.

(8S,20R)-de-A, B-8-hydroxy-20-(2-triethylsilyloxy-ethyl)-pregnane (5)

To a solution of diol 4 (50 mg, 0.22 mmol) in anhydrous $CH_2Cl_2$ (5 mL) at $0°$ C. was added triethylamine (95 µL, 0.67 mmol) followed by triethylsilylchloride (TESCI, 40 µL, 0.22 mmol). The solution was stirred at $0°$ C. for 30 minutes and then quenched with water. The mixture was extracted with $CH_2Cl_2$, and the combined organic phases were dried over $MgSO_4$, filtered, and concentrated to give a residue that was chromatographed on silica gel column (30% EtOAc/hexanes) to afford the O-silylated compound 5 (68 mg, 0.18 mmol, 81%): $[α]^{20}_D$+31.2° (c 1.45, $CHCl_3$); $^1H$ NMR ($CDCl_3$, 400 MHz) δ 4.08 (s, 1H), 3.68 (m, 1H), 3.59 (m, 1H), 1.99 (m, 1H), 0.97 (t, J=7.9 Hz, 9H), 0.91 (s, 3H), 0.60 (q, J=7.9 Hz, 6H); $^{13}C$ NMR ($CDCl_3$) δ 69.45, 60.95, 56.84, 52.60, 41.89, 40.35, 38.86, 33.53, 32.47, 27.19, 22.52, 18.91, 17.41, 13.41, 6.56, 5.78; exact mass calculated for $C_{20}H_{40}O_2Si$ $[M]^+$ 340.2798, found 340.2803.

(20R)-de-A,B-20-(2-triethylsilyloxyethyl)-pregnan-8-one (6)

To a solution of alcohol 5 (41 mg, 0.12 mmol) in $CH_2Cl_2$ (10 mL) were added pyridinium p-toluene sulfonate (PPTS) (10 mg, 0.02 mmol) and pyridinium dichromate (PDC, 0.231 g, 0.60 mmol) at room temperature. After being stirred 6 hours at room temperature, the mixture was passed through 2 cm of flash silica gel pad and washed with EtOAc. The filtrate was concentrated and chromatographed with 20% EtOAc in hexanes to give desired ketone 6 (31 mg, 0.091 mmol, 76%) as a colorless oil. For analytical purpose a sample of ketone 6 was further purified by HPLC (Zorbax Silica, 250/9.4 mm, 10% EtOAc/hexane, 5 mL/minute, Rv=23 mL); $^1H$ NMR ($CDCl_3$, 600 MHz) δ 3.67 (ddd J=10.2, 8.4, 4.8 Hz, 1H), 3.59 (ddd, J=10.2, 7.8, 7.2 Hz, 1H), 2.43 (dd, J=12.0, 7.2 Hz, 1H), 0.95 (d, J=6.6 Hz, 3H) 0.94 (t, J=7.8 Hz, 9H) 0.62 (s, 3H), 0.57 (q, J=7.8 Hz, 6H), $^{13}C$ NMR ($CDCl_3$) δ 212.09, 61.99, 60.72, 56.89, 49.94, 40.97, 38.95, 38.79, 32.64, 27.51, 24.04, 19.08, 19.03, 12.41, 6.80, 4.42; exact mass calculated for $C_{18}H_{33}O_2Si$ $[M-C2H5]^+$ 309.2250, found 309.2252.

(7E)-(1R,3R,20R)-1,3-di-(tert-butyldimethylsilyloxy)-2-methylene-9,10-seco-19-nor-20-(2-triethylsilyloxyethyl)-5,7-pregnandiene (7)

To a solution of phosphine oxide H (89 mg, 0.15 mmol) in anhydrous THF (600 μL) at −20° C. was slowly added PhLi (130 μL, 0.15 mmol) under argon with stirring. The solution turned deep orange. The mixture was cooled to −78° C., and a precooled (−78° C.) solution of ketone 6 (29 mg, 86 μmol) in anhydrous THF (400 μL) was slowly added. The mixture was stirred under argon at −78° C. for 1 hour and at 0° C. for 18 hours. Ethyl acetate was added, and the organic phase washed with brine, dried (MgSO$_4$), and evaporated. The residue was dissolved in hexane, applied on a silica Sep-Pack cartridge, and washed with 0.5% EtOAc in hexanes to give the 19-norvitamin derivative 7 (48 mg, 79%). The Sep-Pack was then washed with ethyl acetate to recover diphenylphosphine oxide (20 mg). $^1$H NMR (CDCl$_3$, 900 MHz) δ 6.21 (d, J=11.2 Hz, 1H, 6-H), 5.83 (d, J=11.2 Hz, 1H, 7-H), 4.97 (s, 1H, =CH$_2$), 4.92 (s, 1H, =CH$_2$), 4.42 (m, 2H, 1β- and 3α-H), 3.68 (ddd, J=10.4, 8.1, 4.5 Hz, 1H), 3.59 (ddd, J=10.4, 7.2, 7.2 Hz, 1H), 2.82 (br d, J=12.6 Hz, 1H), 2.51 (dd, J=13.5, 5.4 Hz, 1H), 2.46 (dd, J=12.6, 4.5 Hz, 1H), 2.33 (dd, J=13.5, 3.6 Hz, 1H), 2.18 (dd, J=11.7, 8.1 Hz, 1H) 0.96 (t, J=8.1 Hz, 9H, SiCH$_2$CH$_3$) 0.94 (d, J=6.3 Hz, 3H), 0.89 (s, 9H, Si-t-Bu), 0.86 (s, 9H, Si-t-Bu), 0.60 (q, J=8.1 Hz, 6H, SiCH$_2$), 0.54 (s, 3H, 18-H$_3$), 0.08, 0.06, 0.04, and 0.02 (each s, each 3H, 4×SiCH$_3$); $^{13}$C NMR (CDCl$_3$) δ 153.22, 141.37, 132.98, 122.63, 116.37, 106.48, 72.73, 71.88, 61.24, 56.96, 56.52, 47.83, 45.95, 40.80, 39.27, 38.80, 33.50, 28.97, 27.93, 26.06, 26.00, 23.65, 22.47, 19.47, 18.47, 18.39, 12.22, 7.03, −4.63 (2×SiMe), −4.68 (SiMe), −4.87 (SiMe); exact mass calculated for C$_{41}$H$_{78}$O$_3$Si$_3$ [M]$^+$ 702.5259, found 702.5286.

(7E)-(1R,3R,20R)-1,3-di-(tert-butyldimethylsilyloxy)-2-methylene-9,10-seco-19-nor-20-(2-hydroxyethyl)-5,7-pregnandiene (8)

To a solution of 7 (48 mg, 68 μmol) in benzene (2 mL) was added AcOH/THF/H$_2$O (8:8:1, 8 mL) at 0° C., and was stirred at the same temperature for 3 hours. To the mixture was added saturated aqueous NaHCO$_3$ solution, and the aqueous layer was extracted with EtOAc. The organic layer washed with saturated aqueous NaCl solution, dried over MgSO$_4$, and concentrated. The residue was chromatographed on silica column (5% EtOAc/hexanes) to give the desired alcohol 8. (32 mg, 54 μmol, 80%); [α]$^{20}_D$ +29.2° (c 1.11, CHCl$_3$) $^1$H NMR (CDCl$_3$, 800 MHz) δ 6.19 (d, J=11.2 Hz, 1H, 6-H), 5.82 (d, J=11.2 Hz, 1H, 7-H), 4.95 (s, 1H, =CH$_2$), 4.90 (s, 1H, =CH$_2$), 4.40 (m, 2H, 10- and 3α-H), 3.71 (m, 1H), 3.63 (m, 1H), 2.82 (br d, J=12.8 Hz, 1H), 2.50 (dd, J=13.6, 6.4 Hz, 1H), 2.44 (dd, J=12.8, 4.0 Hz, 1H), 2.30 (dm, J=10.4, Hz, 1H), 2.16 (dd, J=12.8, 8.8, 1H), 0.95 (d, J=7.2 Hz, 3H), 0.88 (s, 9H, Si-t-Bu), 0.84 (s, 9H, Si-t-Bu), 0.54 (s, 3H), 0.059, 0.044, 0.028, and 0.003 (each s, each 3H, 4×SiCH$_3$), $^{13}$C NMR (CDCl$_3$) δ 141.01, 132.85, 125.51, 122.37, 116.21, 106.26, 72.54, 71.61, 60.93, 56.78, 56.27, 47.62, 45.72, 40.59, 38.95, 38.55, 33.25, 28.72, 27.81, 25.84, 25.78, 23.40, 22.22, 18.99, 18.25, 18.16, 12.04, −4.86 (2×SiMe), −4.91 (SiMe), −5.10 (SiMe); exact mass calculated for C$_{35}$H$_{65}$O$_3$Si$_2$ [MH]$^+$ 589.4472, found 589.4472.

(7E)-(1R,3R,20R)-1,3-di-(tert-butyldimethylsilyloxy)-2-methylene-9,10-seco-19-nor-20-(2-formylmethyl)-5,7-pregnandiene (9)

To a solution of DMSO (100 μL, 1.35 mmol) in CH$_2$Cl$_2$ (5 mL) at −60° C. oxalyl chloride (65 μL, 0.71 mmol) was added. After 2 minutes, a −60° C. solution of the primary alcohol 8 (32 mg, 55 μmol) in CH$_2$Cl$_2$ (3 mL) was added via cannula. The resulting mixture was stirred at −60° C. for 1 hour, quenched with Et$_3$N (0.400 mL, 2.82 mmol), and warmed up to room temperature. Upon dilution with H$_2$O, the extraction mixture was extracted with CH$_2$Cl$_2$, dried (MgSO$_4$), filtered, concentrated, and purified by flash column chromatography (2-5% EtOAc/hexanes) to give the desired aldehyde 9 (25 mg, 0.55 mmol, 78%) [α]$^{20}_D$ −8.4° (c 1.25, CHCl$_3$); $^1$H NMR (CDCl$_3$, 600 MHz) δ 9.75 (dd, J=3.6, 1.8 Hz, 1H), 6.20 (d, J=11.4 Hz, 1H, 6-H), 5.83 (d, J=11.4 Hz, 1H, 7-H), 4.96 (s, 1H, =CH$_2$), 4.91 (s, 1H, =CH$_2$), 4.41 (m, 2H, 1β- and 3α-H), 2.81 (dd, J=12.6, 4.2 Hz, 1H), 2.50 (dd, J=13.2, 6.0 Hz, 1H), 2.47 (m, 2H), 2.45 (dd, J=12.6, 4.8 Hz, 1H), 2.31 (dd, J=13.2, 3.0 Hz, 1H), 1.02 (d, J=6.6 Hz, 3H), 0.88 (s, 9H, Si-t-Bu), 0.85 (s, 9H, Si-t-Bu), 0.58 (s, 3H), 0.07, 0.05, 0.03, and 0.01 (each s, each 3H, 4×SiCH$_3$); $^{13}$C NMR (CDCl$_3$) δ 203.58, 153.13, 140.80, 133.32, 122.50116.61, 106.54, 72.74, 71.81, 56.45, 51.06, 47.84, 45.94, 40.64, 38.78, 32.17, 32.04, 28.86, 28.14, 26.05, 26.00, 23, 54, 22.38, 20.35, 18.47, 18.39, 12.29, −4.63 (3×SiMe), −4.89 (SiMe); exact mass calculated for C$_{35}$H$_{62}$O$_3$Si$_2$ [M]+586.4238, found 586.4247.

(7E)-(1R,3R,20R)-1,3-di-(tert-butyldimethylsilyloxy)-2-methylene-9,10-seco-19-nor-20-[(2S)-hydroxy-4-methoxycarbonyl-4-penten-1-yl]-5,7-pregnandiene (10) and (7E)-(1R,3R,20R)-1,3-di-(tert-butyldimethylsilyloxy)-2-methylene-9,10-seco-19-nor-20-[(2R)-hydroxy-4-methoxycarbonyl-4-penten-1-yl]-5,7-pregnandiene (11)

To a solution of 9 (25 mg, 425 μmol) in saturated aqueous NH$_4$Cl solution/THF (5:1, 3 mL) were added methylbromomethylacrylate (10 μL, 85 μmol) (commercially available from Sigma-Aldrich) and activated Zn dust (11 mg, 0.17 mmol) at 0° C., and the mixture was stirred at the same temperature for 1.5 hours. The mixture was diluted with EtOAc. The organic layer washed with saturated aqueous NaCl solution, dried over MgSO$_4$, and concentrated. The residue was purified by flash column chromatography on silica gel (5% EtOAc/hexanes) to give 10 (5 mg, 7.3 μmol, 57%) and 11 (4 mg, 5.5 μmol, 43%) as colorless oils, respectively.

10: $^1$H NMR (CDCl$_3$, 400 MHz) δ 6.25 (s, 1H, =CH$_2$), 6.21 (d, J=11.2 Hz, 1H, 6-H), 5.84 (d, J=11.2 Hz, 1H, 7-H), 5.67 (s, 1H, =CH$_2$), 4.97 (s, 1H, =CH$_2$), 4.91 (s, 1H, =CH$_2$), 4.42 (m, 2H, 1β- and 3α-H), 3.87 (m, 1H, CH—OH), 3.77 (s, 3H, —CO$_2$CH$_3$), 2.82 (br d, J=11.3, 1H), 2.56-2.44 (m, 3H), 2.40-2.25 (m, 2H), 2.18 (m, 1H), 0.97 (d, J=6.6 Hz, 3H), 0.90 (s, 9H, Si-t-Bu), 0.85 (s, 9H, Si-t-Bu), 0.57 (s, 3H), 0.08, 0.06, 0.05, and 0.02 (each s, each 3H, 4×SiCH$_3$); $^{13}$C NMR (CDCl$_3$) δ 168.31, 153.19, 141.28, 137.76, 133.03, 127.92, 122.58, 116.41, 106.44, 72.79, 71.78, 67.85, 57.35, 56.54, 52.28, 47.85, 46.00, 43.93, 41.78, 40.86, 38.72, 33.09, 28.94, 28.08, 26.04, 25.97, 23.62, 22.44, 18.87, 18.45, 18.35, 12.35, −4.67 (SiMe), −4.90 (3×SiMe); exact mass calculated for C$_{40}$H$_{70}$O$_5$Si$_2$Na [M+Na]$^+$ 709.4660, found 709.4680.

11: $^1$H NMR (CDCl$_3$, 400 MHz) δ 6.29 (s, 1H, =CH$_2$), 6.22 (d, J=11.1 Hz, 1H, 6-H), 5.84 (d, J=11.1 Hz, 1H, 7-H), 5.70 (s, 1H, =CH$_2$), 4.98 (s, 1H, =CH$_2$), 4.93 (s, 1H, =CH$_2$), 4.43 (m, 2H, 1β- and 3α-H), 3.90 (m, 1H, CH—OH), 3.79 (s, 3H, —CO$_2$CH$_3$), 2.84 (br d, J=12.1 Hz, 1H), 2.71 (dd, J=13.8, 1.7 Hz, 1H), 2.56-2.42 (m, 2H), 2.34 (m, 1H), 1.03 (d, J=6.4 Hz, 3H), 0.90 (s, 9H, Si-t-Bu), 0.87 (s, 9H, Si-t-Bu), 0.57 (s, 3H), 0.09, 0.08, 0.06, and 0.04 (each s, each 3H, 4×SiCH$_3$); $^{13}$C NMR (CDCl$_3$), δ 168.30, 153.17, 141.23, 137.77, 133.04, 128.07, 122.58, 116.41, 106.46, 72.72, 71.83, 69.45, 57.47, 56.43, 52.28, 47.80, 45.91, 44.13, 40.81, 40.27, 38.77, 34.39, 28.93, 28.12, 26.03, 25.98, 23.61, 22.42, 19.55, 18.74, 18.37, 12.29, −4.67 (3×SiMe), −4.88 (SiMe); exact mass calculated for C$_{40}$H$_{70}$O$_5$Si$_2$ [M]$^+$ 686.4762, found 686.4789.

(23S)-25-Dehydro-2-Methylene-19-nor-α-hydroxyvitamin D$_3$-26,23-lactone (HLV)

To a suspension of NaH (60% oil dispersion, 4 mg, 100 µmol) was added a solution of 10 (5 mg, 7 µmol) in THF (3 mL) at 0° C., and the mixture was stirred at the same temperature for 30 minutes. To the mixture was added saturated aqueous NH$_4$Cl solution, and the aqueous layer was extracted with Et$_2$O. The organic layer were combined and washed with saturated aqueous NaCl solution, dried over MgSO$_4$, and concentrated. The residue was purified by flash column chromatography on silica gel (5% EtOAc/hexanes) to give protected vitamin 12 (4 mg, 6 µmol, 81%) as a colorless oil. $^1$H NMR (CDCl$_3$, 900 MHz) δ 6.22 (dd, J=2.7, 2.7, 1H, =CH$_2$), 6.20 (d, J=11.3 Hz, 1H, 6-H), 5.82 (d, J=11.3 Hz, 1H, 7-H), 5.61 (dd, J=2.7, 2.7 Hz, 1H, =CH$_2$), 4.96 (s, 1H, =CH$_2$), 4.90 (s, 1H, =CH$_2$), 4.64 (m, 1H, CH—O—), 4.42 (m, 2H, 1β- and 3α-H), 3.06 (dddd, J=17.1, 7.2, 2.7, 2.7 Hz, 1H) 2.81 (dm, J=12.6 Hz, 1H), 2.54 (dd, J=12.6, 5.4 Hz, 1H), 2.52 (dddd, J=17.1, 5.4, 3.6, 2.7 Hz, 1H), 2.46 (dd, J=13.5, 5.4 Hz, 1H), 2.28 (dd, J=13.5, 2.7 Hz, 1H), 2.16 (dd, J=12.6, 8.1 Hz, 1H), 2.01 (dm, J=12.6 Hz, 1H), 1.99 (dd, J=12.6, 7.2 Hz, 1H), 1.01 (d, J=6.3 Hz, 3H), 0.89 (s, 9H, Si-t-Bu), 0.85 (s, 9H, Si-t-Bu), 0.55 (s, 3H), 0.07, 0.05, 0.04, and 0.01 (each s, each 3H, 4×SiCH$_3$); $^{13}$C NMR (CDCl$_3$) δ 170.66, 153.18, 140.96, 135.05, 133.24, 122.51, 122.11, 116.57, 106.44, 75.40, 72.82, 71.73, 57.07, 56.49, 47.88, 45.98, 43.73, 40.84, 38.70, 34.72, 33.28, 28.90, 27.94, 26.05, 25.96, 23.57, 22.43, 18.81, 18.47, 18.36, 12.31, −4.67 (3×SiMe), −4.88 (SiMe); exact mass calculated for C$_{39}$H$_{66}$O$_4$Si$_2$Na [M+Na]$^+$ 677.4397, found 677.4407.

To a solution of 12 (3 mg, 5.3 µmol) in MeCN (1 mL) was added HF/MeCN (1:9, 1 mL) at 0° C., and the mixture was stirred at the same temperature for 30 minutes. To the mixture was added saturated aqueous NaHCO$_3$ solution, and the aqueous layer was extracted with EtOAc. The organic layer washed with saturated aqueous NaCl solution, dried over MgSO$_4$, and concentrated. The residue was purified by flash column chromatography on silica gel (20% EtOAc/hexanes) to give HLV (2 mg, 4.6 µmol, 88%) as a colorless oil. For analytical purpose a sample of the final product HLV was further purified by HPLC (Zorbax Eclipse XDB-C18, 15% MeOH/H$_2$O, 3 mL/minute, Rv=21.8 mL); UV (in ethanol) λ$_{max}$ 243, 251, 261; $^1$H NMR (CDCl$_3$, 800 MHz) δ 6.34 (d, J=11.2 Hz, 1H, 6-H), 6.23 (dd, J=2.4, 2.4 Hz, 1H, =CH$_2$), 5.88 (d, J=11.2 Hz, 1H, 7-H), 5.62 (dd, J=2.4, 2.4 Hz, 1H, =CH$_2$), 5.11 (s, 1H, =CH$_2$), 5.09 (s, 1H, =CH$_2$), 4.65 (m, 1H, —CH—O—), 4.49 (m, 1H), 4.46 (m, 1H), 3.07 (dddd, J=16.8, 8.0, 2.4, 2.4 Hz, 1H) 2.87 (dd, J=13.6, 4.8 Hz, 1H), 2.81 (dm, J=12.8 Hz, 1H), 2.57 (dd, J=13.6, 4.0 Hz, 1H), 2.53 (dddd, J=16.8, 5.6, 3.2, 3.2 Hz, 1H), 2.33 (dd, 13.6, 5.6 Hz, 1H), 2.27 (dd, J=12.8, 8.0 Hz, 1H), 2.01 (m, 2H), 1.02 (d, J=6.4 Hz, 3H), 0.57 (s, 3H); exact mass calculated for C$_{27}$H$_{38}$O$_4$Na [M+Na]$^+$ 449.2668, found 449.2666.

(23R)-25-Dehydro-2-Methylene-19-nor-1α-hydroxyvitamin D$_3$-26,23-lactone (GC-3)

To a suspension of NaH (60% oil dispersion, 4 mg, 100 µmol) was added a solution of 11 (3 mg, 5.1 µmol) in THF (3 mL) at 0° C., and the mixture was stirred at the same temperature for 30 minutes. To the mixture was added saturated aqueous NH$_4$Cl solution, and the aqueous layer was extracted with Et$_2$O. The organic layer were combined and washed with saturated aqueous NaCl solution, dried over MgSO$_4$, and concentrated. The residue was purified by flash column chromatography on silica gel (5% EtOAc/hexanes) to give protected vitamin 13 (1.5 mg, 2.3 µmol, 45%) as a colorless oil. $^1$H NMR (CDCl$_3$, 900 MHz) δ 6.21 (dd, J=2.7, 2.7 Hz, 1H, =CH$_2$), 6.20 (d, J=10.8 Hz, 1H, 6-H), 5.82 (d, J=10.8 Hz, 1H, 7-H), 5.61 (dd, J=2.7, 2.7 Hz, 1H, =CH$_2$), 4.96 (s, 1H, =CH$_2$), 4.91 (s, 1H, =CH$_2$), 4.59 (ddt, J=14.4, 14.4, 7.2 Hz, 1H, —CH—O—), 4.41 (m, 2H, 1β- and 3α-H), 3.04 (dddd, J=16.7, 7.2, 2.7, 1.8 Hz, 1H) 2.81 (dm, J=12.6 Hz, 1H), 2.54 (dddd, J=16.7, 6.3, 3.6, 2.7 Hz, 1H), 2.49 (dd, J=13.5, 6.3 Hz, 1H), 2.45 (dd, J=13.5, 4.5 Hz 1H), 2.32 (dd, J=13.5, 3.6 Hz, 1H), 2.17 (dd, J=13.5, 9.0 Hz, 1H), 1.02 (d, J=7.2 Hz, 3H), 0.88 (s, 9H, Si-t-Bu), 0.85 (s, 9H, Si-t-Bu), 0.55 (s, 3H), 0.07, 0.05, 0.03, and 0.01 (each s, each 3H, 4×SiCH$_3$); $^{13}$C NMR (CDCl$_3$) δ 170.57, 153.12, 140.92, 134.94, 133.21, 122.52, 122.07, 116.55, 106.51, 72.71, 71.83, 56.80, 56.35, 47.80, 45.87, 42.54, 40.72, 38.79, 34.27, 33.90, 28.87, 28.24, 25.99 (2×-t-Bu-Si), 23.54, 22.38, 19.48, 18.45, 12.23, −4.66 (3×SiMe), −4.90 (SiMe); exact mass calculated for C$_{39}$H$_{66}$O$_4$Si$_2$Na [M+Na]$^+$ 677.4397, found 677.4407.

To a solution of 13 (2 mg, 4 µmol) in MeCN (1 mL) was added HF/MeCN (1:9, 1 mL) at 0° C., and the mixture was stirred at the same temperature for 30 minutes. To the mixture was added saturated aqueous NaHCO$_3$ solution, and the aqueous layer was extracted with EtOAc. The organic layer washed with saturated aqueous NaCl solution, dried over MgSO$_4$, and concentrated. The residue was purified by flash column chromatography on silica gel (20% EtOAc/hexanes) to give GC-3 (1 mg, 2 µmol, 60%) as a colorless oil. For analytical purpose a sample of the final product GC-3 was further purified by HPLC (Zorbax Eclipse XDB-C18, 15% MeOH/H$_2$O, 3 mL/minute, Rv=22.6 mL)); UV (in ethanol) λ$_{max}$ 243, 251, 261; $^1$H NMR (CDCl$_3$, 800 MHz) δ 6.35 (d, J=11.2 Hz, 1H, 6-H), 6.22 (dd, J=2.4, 2.4 Hz, 1H, =CH$_2$), 5.88 (d, J=11.2 Hz, 1H, 7-H), 5.62 (dd, J=2.4, 2.4 Hz, 1H, =CH$_2$), 5.12 (s, 1H, =CH$_2$), 5.09 (s, 1H, =CH$_2$), 4.59 (ddt, J=14.4, 13.6, 7.2 Hz, 1H, CH—O—), 4.49 (m, 1H), 4.47 (m, 1H), 3.05 (dddd, J=16.8, 7.2, 2.4, 2.4 Hz, 1H) 2.84 (dd, J=13.6, 4.0 Hz, 1H), 2.81 (dm, J=15.2 Hz, 1H), 2.58 (dd, J=13.6, 4.0 Hz, 1H), 2.55 (dddd, J=16.8, 6.4, 3.2, 3.2 Hz, 1H), 2.33 (dd, J=13.6, 6.4 Hz, 1H), 2.30 (dd, J=13.6, 8.8 Hz, 1H), 1.03 (d, J=6.4 Hz, 3H), 0.57 (s, 3H); exact mass calculated for C$_{27}$H$_{38}$O$_4$Na [M+Na]$^+$ 449.2668, found 449.2688.

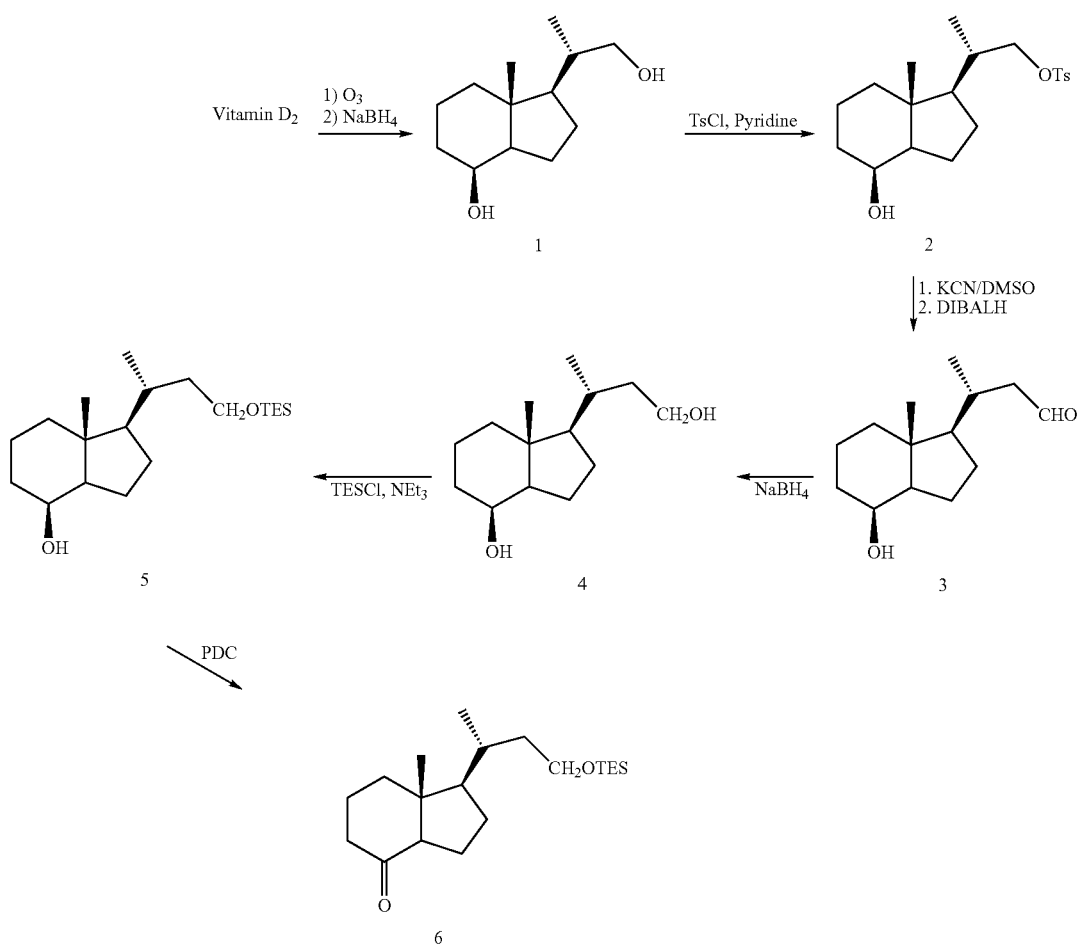
Scheme IIA
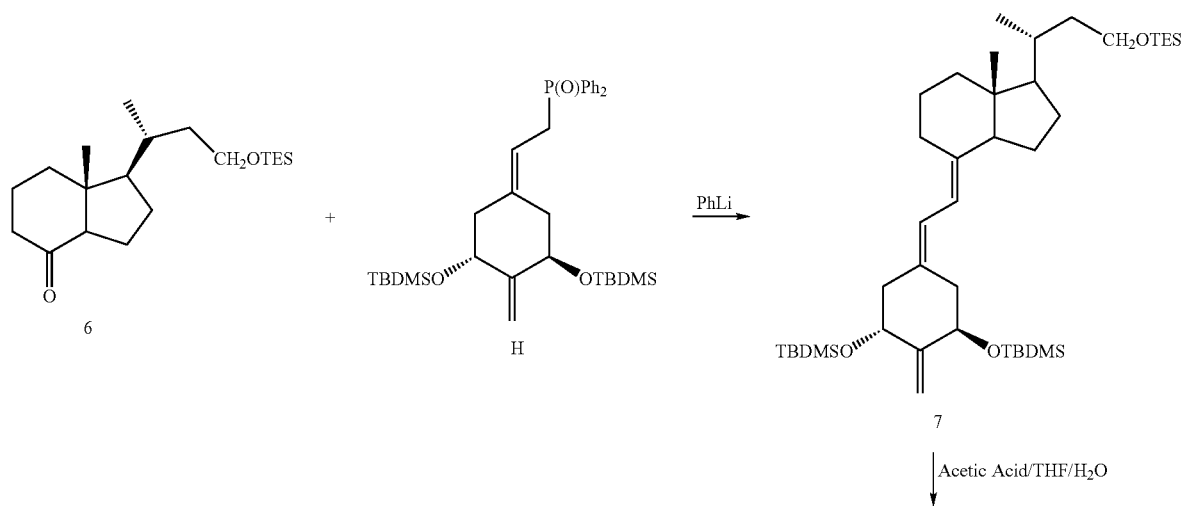
Scheme IIB

19
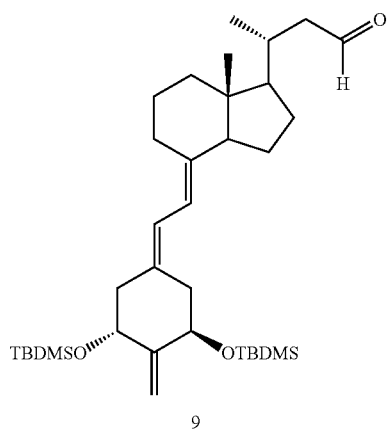
9
20
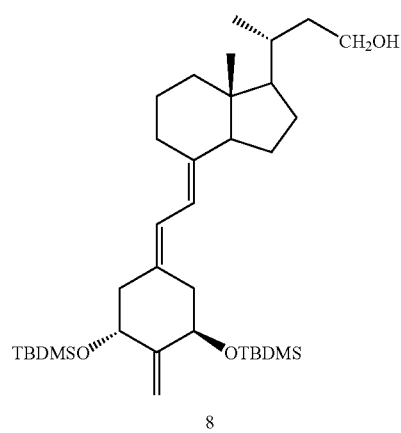
8
Oxalyl Chloride / Swern Oxidation
-continued
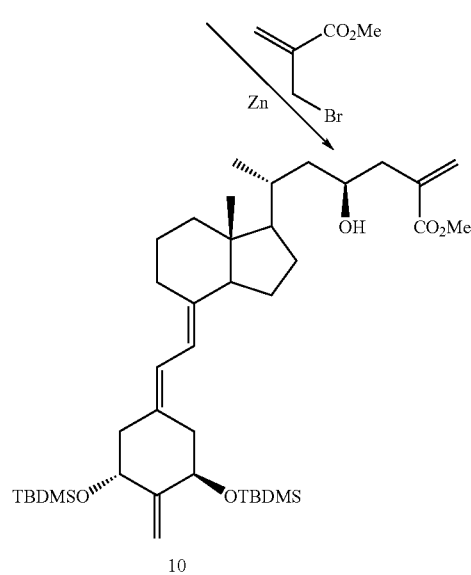
10
+
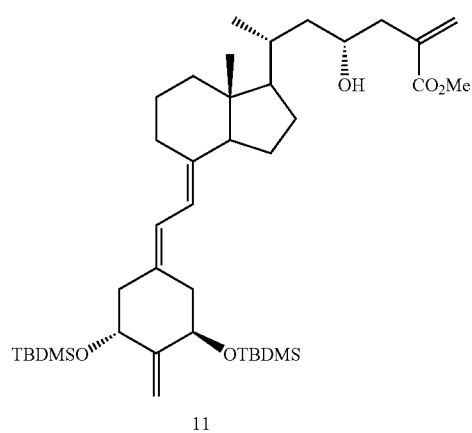
11
Scheme IIC
10 →(NaH/THF)
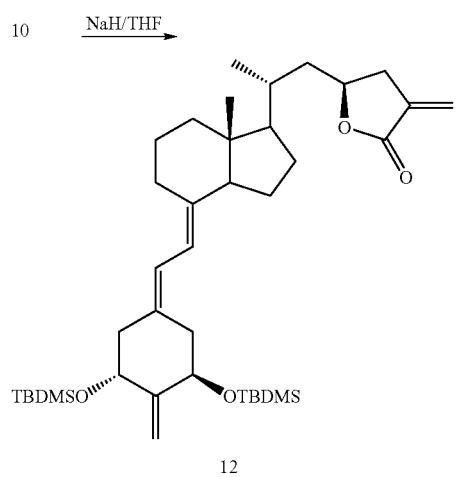
12
-continued
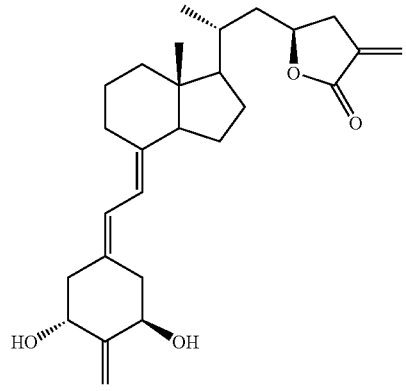
HF/MeCN →
HLV
11 →(NaH/THF)

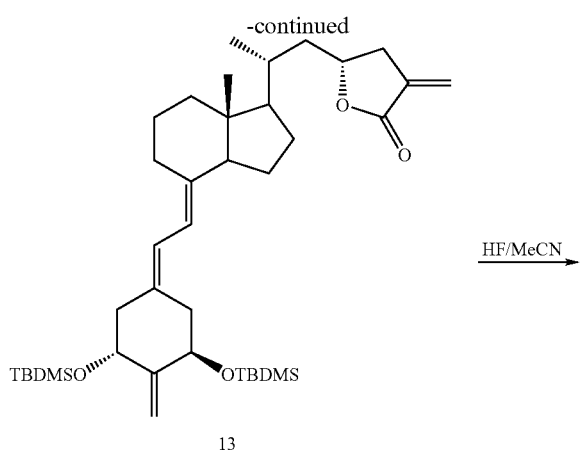

-continued

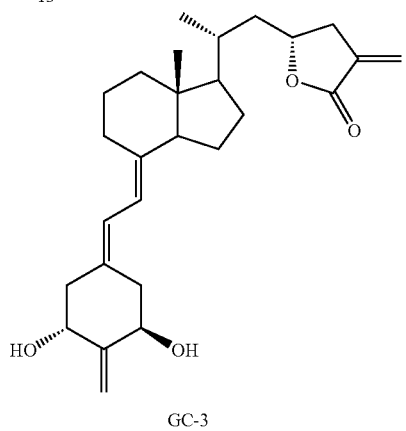

GC-3

Biological Activity

Vitamin D Receptor Binding

Test Material

Protein Source

Full-length recombinant rat vitamin D receptor was expressed in E coli BL21(DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in TEDK$_{50}$ (50 mM Tris, 1.5 mM EDTA, pH 7.4, 5 mM DTT, 150 mM KCl) with 0.1% Chaps detergent. The receptor protein and ligand concentration was optimized such that no more than 20% of the added radiolabeled ligand was bound to the receptor.

Study Drugs

Unlabeled ligands were dissolved in ethanol and the concentrations determined using UV spectrophotometry (1,25 (OH)$_2$D$_3$: molar extinction coefficient=18,200 and $\lambda_{max}$=265 nm; Analogs: molar extinction coefficient=42,000 and $\lambda_{max}$=252 nm). Radiolabeled ligand ($^3$H-1,25(OH)$_2$D$_3$, ~159 Ci/mmol) was added in ethanol at a final concentration of 1 nM.

Assay Conditions

Radiolabeled and unlabeled ligands were added to 100 mcl of the diluted protein at a final ethanol concentration of ≦10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 mL of Biosafe II scintillation cocktail, mixed and placed in a scintillation counter. Total binding was determined from the tubes containing only radiolabeled ligand.

HL-60 Differentiation

Test Material

Study Drugs

The study drugs were dissolved in ethanol and the concentrations determined using UV spectrophotometry. Serial dilutions were prepared so that a range of drug concentrations could be tested without changing the final concentration of ethanol (≦0.2%) present in the cell cultures.

Cells

Human promyelocytic leukemia (HL60) cells were grown in RPMI-1640 medium containing 10% fetal bovine serum. The cells were incubated at 37° C. in the presence of 5% CO$_2$.

Assay Conditions

HL60 cells were plated at $1.2 \times 10^5$ cells/mL. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In Vitro Transcription Assay

Transcription activity was measured in ROS 17/2.8 (bone) cells that were stably transfected with a 24-hydroxylase (24OHase) gene promoter upstream of a luciferase reporter gene (Arbour et al, 1998). Cells were given a range of doses. Sixteen hours after dosing the cells were harvested and luciferase activities were measured using a luminometer. RLU=relative luciferase units.

Antagonism was tested by adding a combination of 1,25 (OH)$_2$D$_3$ and the compound in the same well keeping the final ethanol concentration the same.

Intestinal Calcium Transport and Bone Calcium Mobilization

Male, weanling Sprague-Dawley rats were placed on Diet 11 (Suda et al. J. Nutr. 100:1049, 1970) (0.47% Ca) diet+ vitamins AEK for one week followed by Diet 11 (0.02% Ca)+AEK for 3 weeks. The rats were then switched to a diet containing 0.47% Ca for one week followed by two weeks on a diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method. Antagonism was tested by administering a combination of $1,25(OH)_2D_3$ and the compound to the animal simultaneously.

Figure 2:
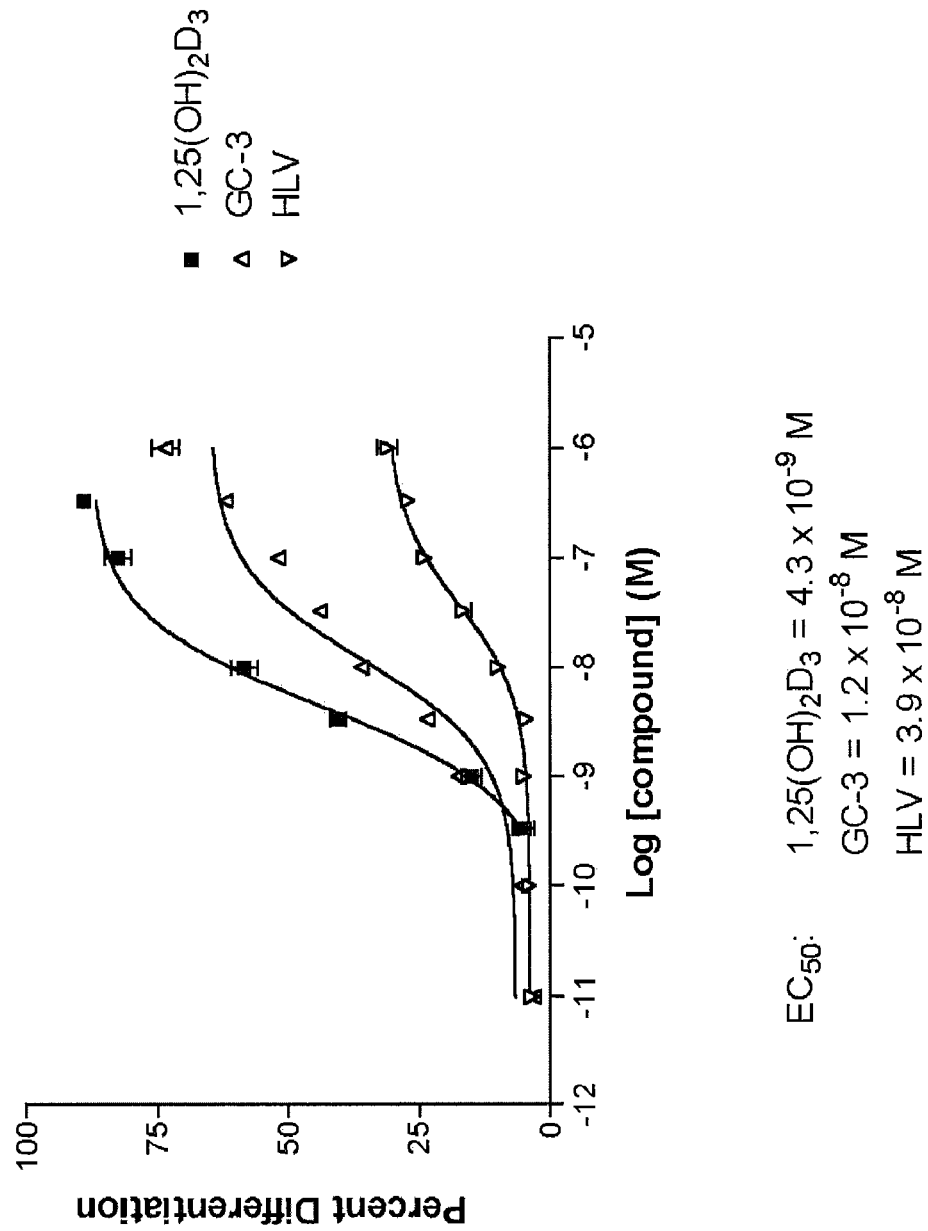
Figure 3:
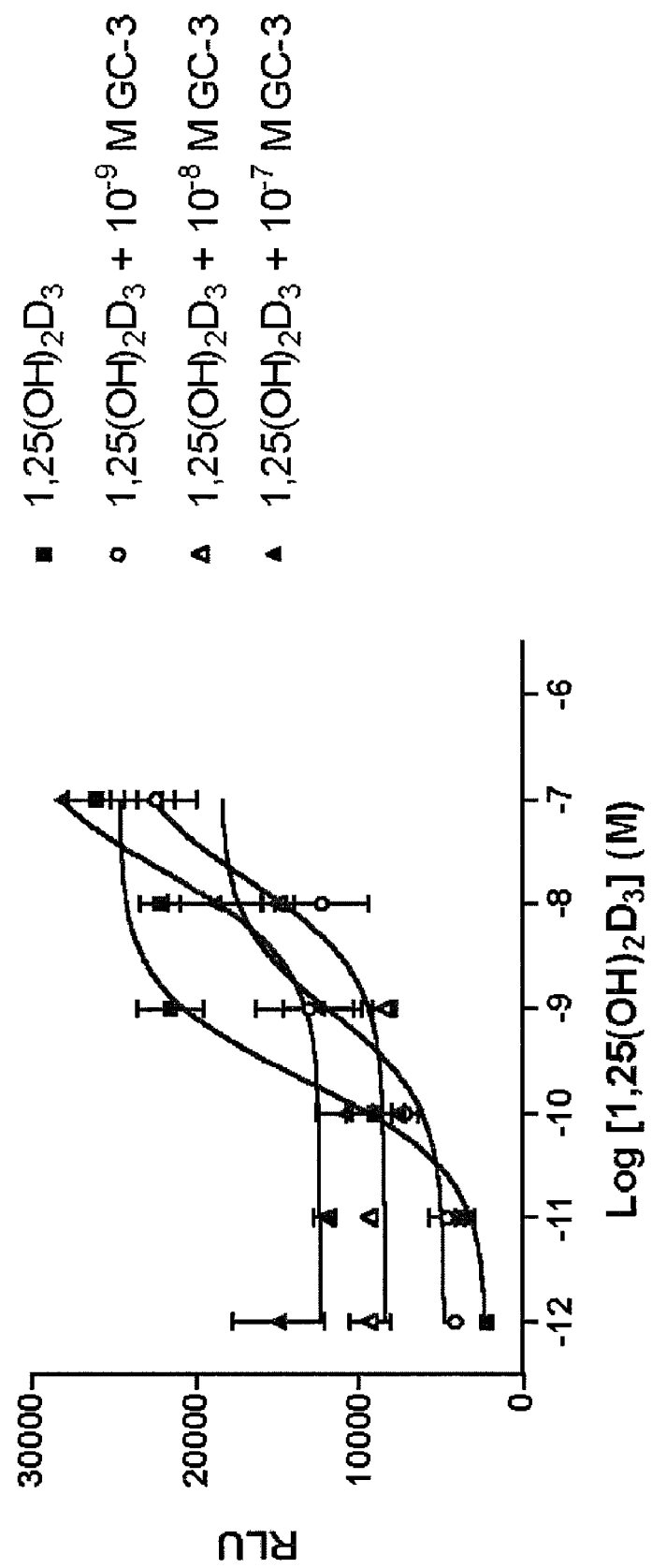
Figure 4:
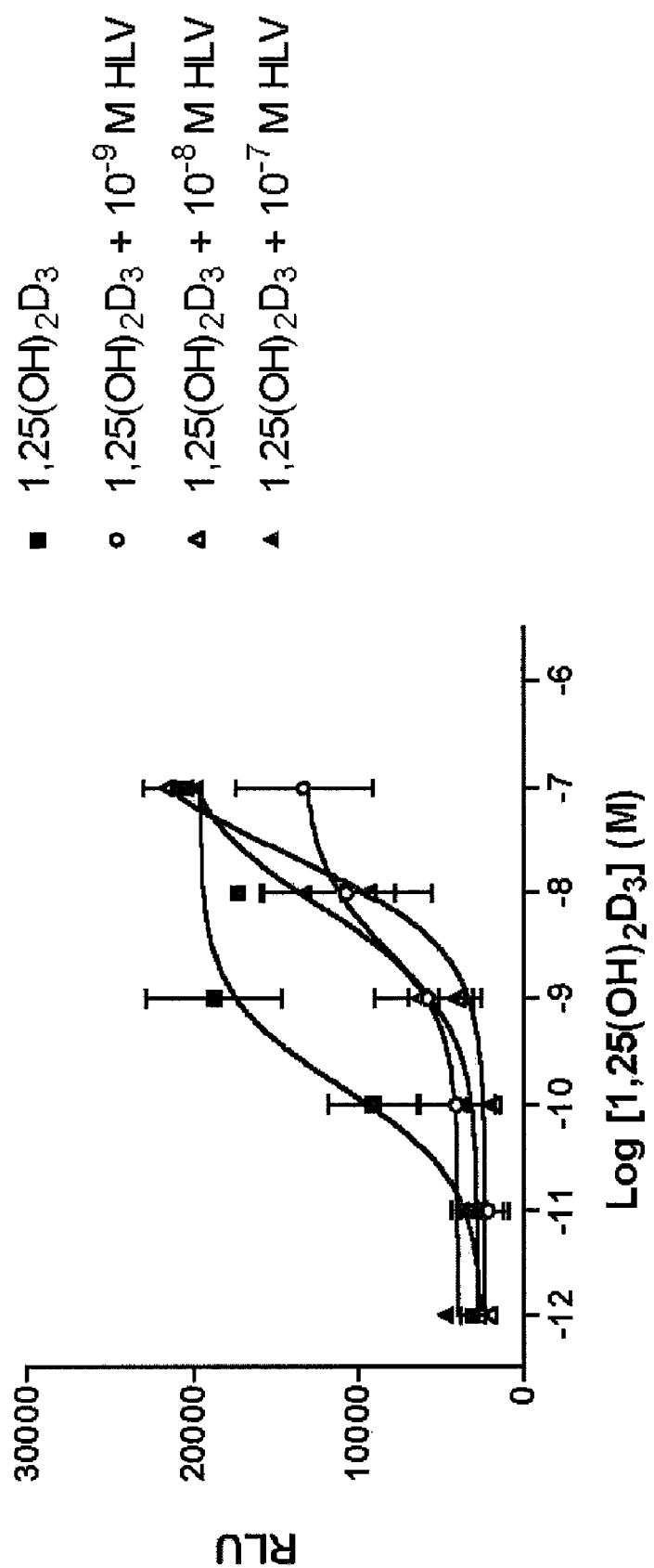
Figure 5:
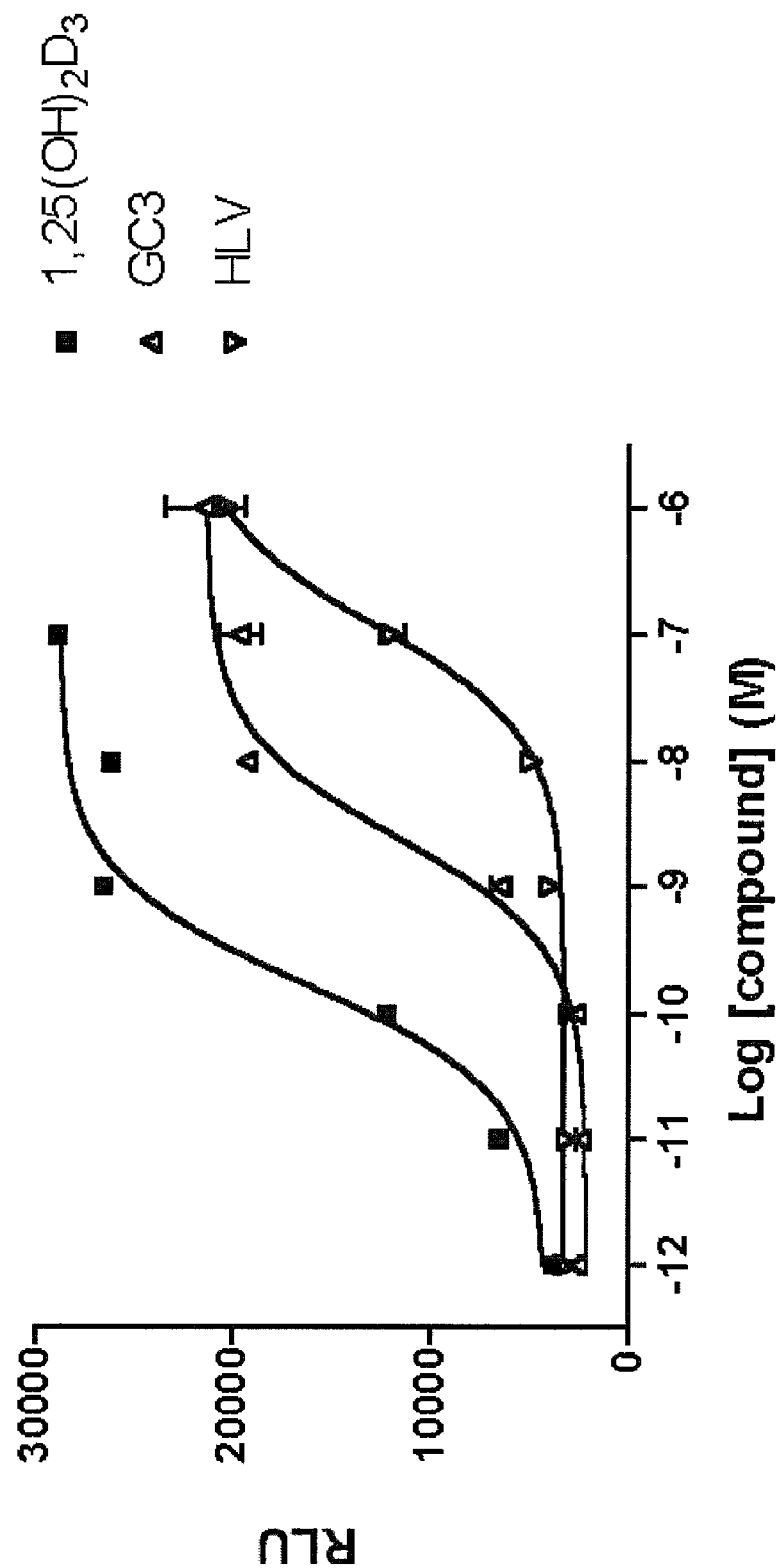
Figure 6:
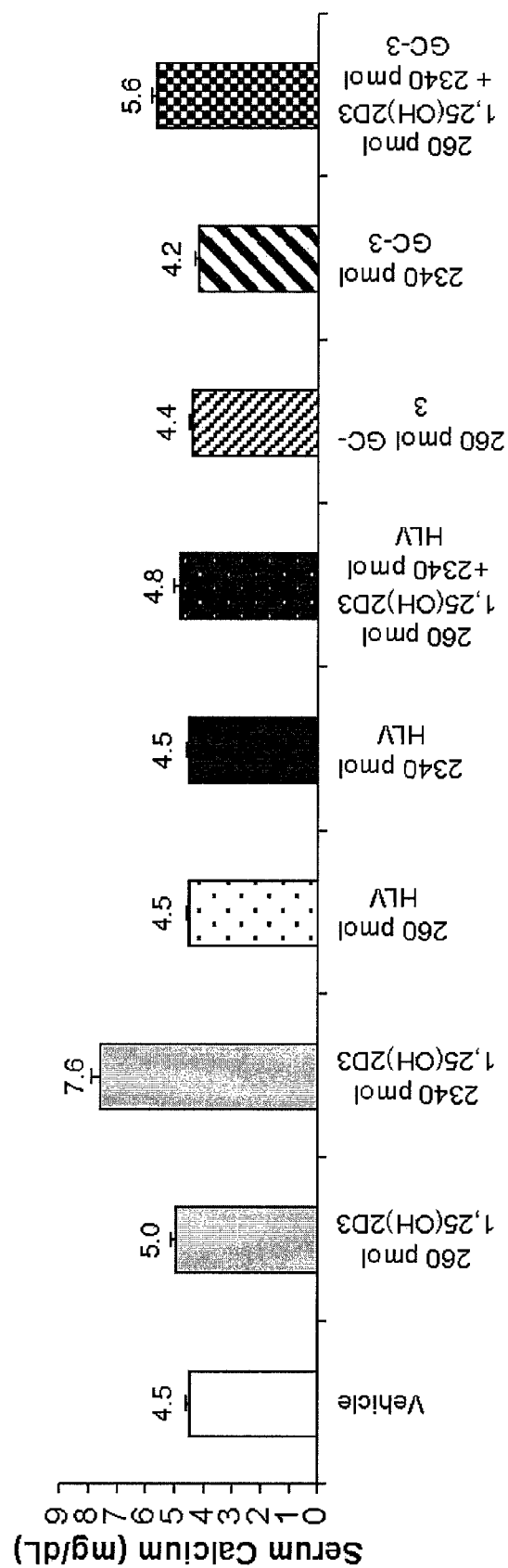
Figure 7:
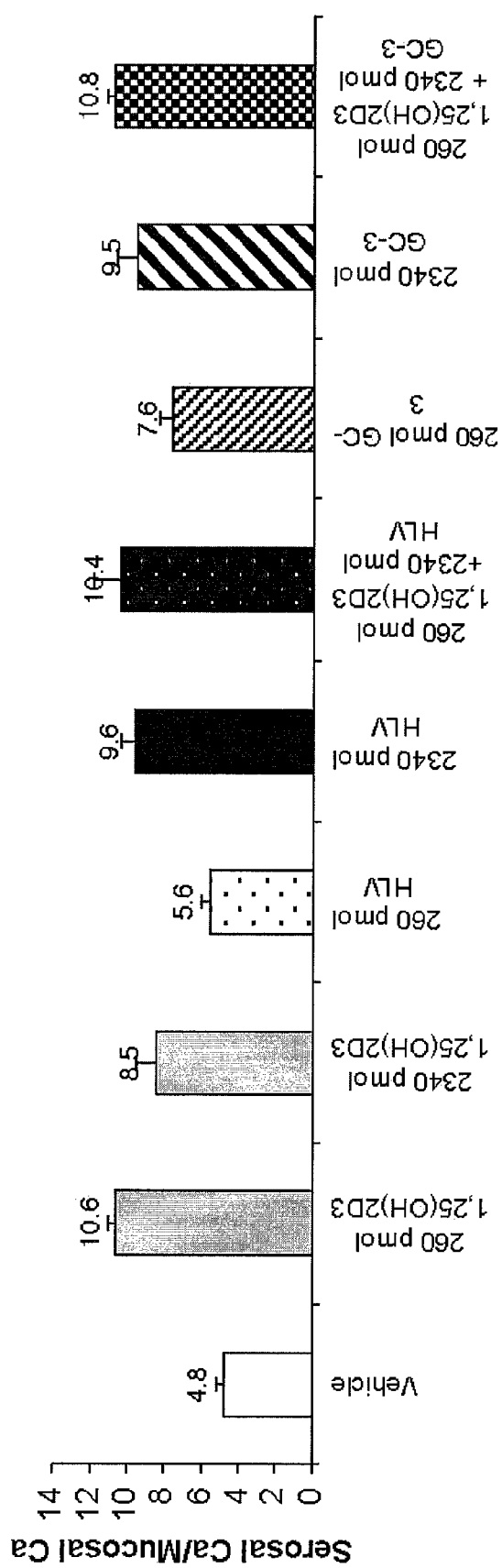

Both GC-3 and HLV bind to the vitamin D receptor, but both of these compounds are less active in this respect than is $1\alpha,25$-dihydroxyvitamin $D_3$ (see FIG. 1). Both GC-3 and HLV also show less activity than $1,25$-$(OH)_2D_3$ in inducing differentiation of HL-60 cells (FIG. 2). GC-3 shows antagonistic activity when administered along with the native hormone ($1\alpha,25$-dihydroxyvitamin $D_3$) as shown in FIGS. 3 and 5, and HLV shows antagonistic activity to an even greater extent as shown in FIGS. 4 and 5. GC-3 and HLV have no calcemic activity when measured by bone calcium mobilization even when given at the dose of 2,340 pmol/day (see FIG. 6). However, both GC-3 and HLV do retain the ability to elevate intestinal calcium transport (FIG. 7). Because these compounds act as antagonists in vitro and weak agonists in vivo, these compounds could serve as useful therapeutic agents when administered locally to some tissues. These compounds may thus find use in therapies for treating asthma, hypercalcemia, eczema, sarcoidosis, and vitamin D intoxication.

The compounds of the invention are useful in applications where antagonization of the vitamin D receptor is desired. Such applications may include the treatment of asthma or eczema in animal subjects suffering from asthma or eczema. Therefore, in some embodiments, a method of preventing or treating asthma or eczema in an animal subject includes administering to the animal subject, an effective amount of the compound or compounds of the invention or a pharmaceutical composition that includes the compound or compounds. Administration of the compound or compounds or the pharmaceutical composition to the subject inhibits or reduces asthma or eczema in the animal subject.

For treatment purposes, the compounds defined by formulas 1A, 1B, 1A1, 1B1, 1A2, and 1B2 may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically acceptable and non-toxic excipients such as stabilizers, anti-oxidants, binders, coloring agents or emulsifying or taste-modifying agents. Pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is hereby incorporated by reference in its entirety and for all purposes as if fully set forth herein.

The compounds may be administered orally, topically, parenterally, rectally, or transdermally. The compounds are advantageously administered by injection or by intravenous infusion or suitable sterile solutions, or in the form of liquid or solid doses via the alimentary canal, or in the form of creams, ointments, patches, or similar vehicles suitable for transdermal applications. In some embodiments, doses of from 0.001 µg to about 1 mg per day of the compound are appropriate for treatment purposes. In some such embodiments an appropriate and effective dose may range from 0.01 µg to 1 mg per day of the compound. In other such embodiments an appropriate and effective dose may range from 0.1 µg to 500 µg per day of the compound. Such doses will be adjusted according to the type of disease or condition to be treated, the severity of the disease or condition, and the response of the subject as is well understood in the art. The compound may be suitably administered alone, or together with another active vitamin D compound.

Compositions for use in the invention include an effective amount of GC-3 and/or HLV as the active ingredient or ingredients, and a suitable carrier. An effective amount of the compound or compounds for use in accordance with some embodiments of the invention will generally be a dosage amount such as those described herein, and may be administered topically, transdermally, orally, nasally, rectally, or parenterally.

The compounds of formula 1A and formula 1B may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art. As noted, the compounds of formula 1A and formula 1B may be present as a mixture of the two compounds. In some mixtures, the mixture may include the compound of formula 1A and the compound of formula 1B. In some embodiments, the mixture includes the compound of formula 1A and the compound of formula 1B, and the ratio of the compound of formula 1A to the compound of formula 1B ranges from 50:50 to 99.9:0.1. In some such embodiments, the ratio of the compound of formula 1A to the compound of formula 1B ranges from 70:30 to 99.9:0.1, from 80:20 to 99.9:0.1, from 90:10 to 99.9:0.1, or from 95:5 to 99.9:0.1. In other embodiments, the mixture includes the compound of formula 1A and the compound of formula 1B, and the ratio of the compound of formula 1B to the compound of formula 1A ranges from 50:50 to 99.9:0.1. In some such embodiments, the ratio of the compound of formula 1B to the compound of formula 1A ranges from 70:30 to 99.9:0.1, from 80:20 to 99.9:0.1, from 90:10 to 99.9:0.1, or from 95:5 to 99.9:0.1.

The compound or compounds may be formulated as creams, lotions, ointments, aerosols, suppositories, topical patches, pills, capsules or tablets, or in liquid form as solutions, emulsions, dispersions, or suspensions in pharmaceutically innocuous and acceptable solvent or oils, and such preparations may contain, in addition, other pharmaceutically innocuous or beneficial components, such as stabilizers, antioxidants, emulsifiers, coloring agents, binders or taste-modifying agents.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100 microns.

The formulations may conveniently be presented in dosage unit form and may be prepared by any of the methods well known in the art of pharmacy. By the term "dosage unit" is meant a unitary, i.e., a single dose which is capable of being administered to a patient as a physically and chemically stable unit dose comprising either the active ingredient as such or a mixture of it with solid or liquid pharmaceutical diluents or carriers.

All references cited herein are specifically incorporated by reference in their entireties and for all purposes as if fully set forth herein.

It is understood that the invention is not limited to the embodiments set forth herein for illustration, but embraces all such forms thereof as come within the scope of the following claims.

The invention claimed is:

1. A method of treating a subject suffering from a biological disorder selected from the group consisting of asthma and eczema, comprising administering an effective amount of a compound of formula 1A1 or 1B1, a mixture thereof, or a pharmaceutical formulation comprising the compound or mixture of compounds and a pharmaceutically acceptable carrier to the subject,

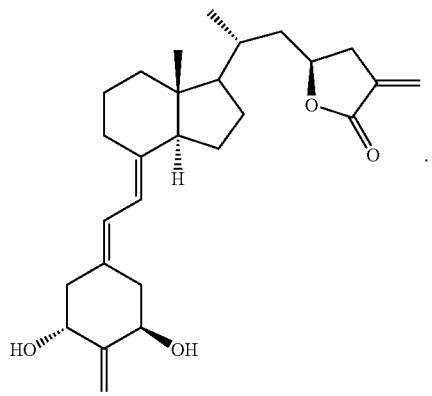

-continued

2. The method of claim 1, wherein the compound or mixture of compounds antagonizes a vitamin D receptor in the subject after administration.

3. The method of claim 1, wherein the biological disorder is asthma.

4. The method of claim 1, wherein the biological disorder is eczema.

5. The method of claim 1, wherein the compound, the mixture of compounds, or the pharmaceutical formulation is administered orally, parenterally, rectally, transdermally, or topically to the subject.

6. The method of claim 1, wherein the compound, the mixture of compounds, or the pharmaceutical formulation is administered by delivering the compound, mixture of compounds or pharmaceutical formulation in an aerosol.

7. The method of claim 1, wherein the compound or the mixture of compounds is administered in a dosage of from 0.01 µg per day to 1 mg per day.

8. The method of claim 1, wherein the compound has the formula 1A2 or 1B2,

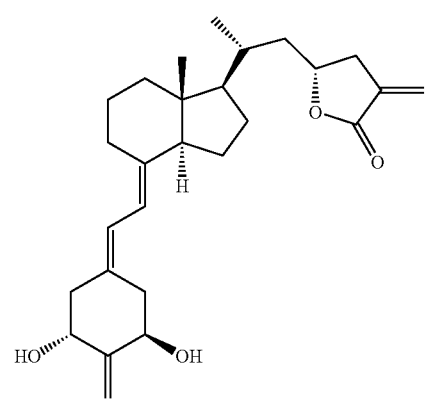

-continued

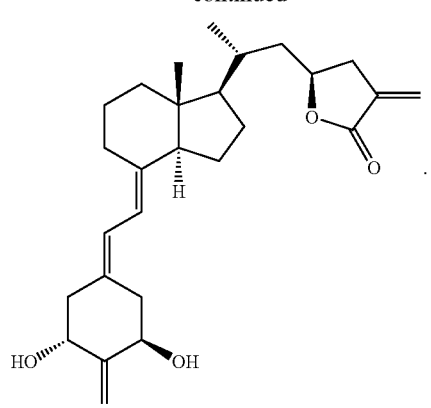

1B2

9. The method of claim 1, wherein the subject is human.

10. A method of treating hypercalcemia, sarcoidosis, or vitamin D intoxication in an animal subject suffering from hypercalcemia, sarcoidosis, or vitamin D intoxication, comprising administering a compound of formula 1A1 or 1B1, a mixture thereof, or a pharmaceutical formulation comprising the compound or mixture of compounds and a pharmaceutically acceptable carrier to the animal subject,

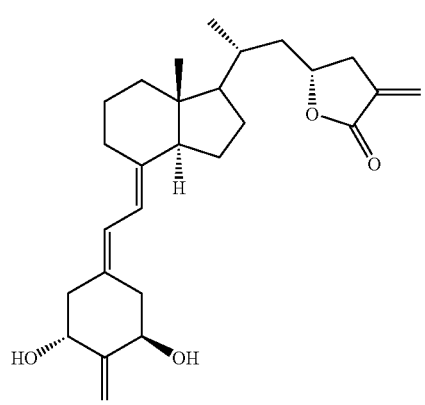

1A1

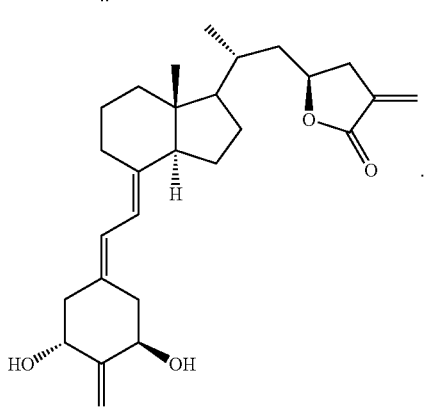

1B1

11. The method of claim 10, wherein the compound, the mixture of compounds, or the pharmaceutical formulation is administered using an inhaler or nebulizer.

12. The method of claim 10, wherein the compound is administered orally, parenterally, rectally, transdermally, or topically to the subject.

13. The method of claim 10, wherein the compound has the formula 1A2 or 1B2,

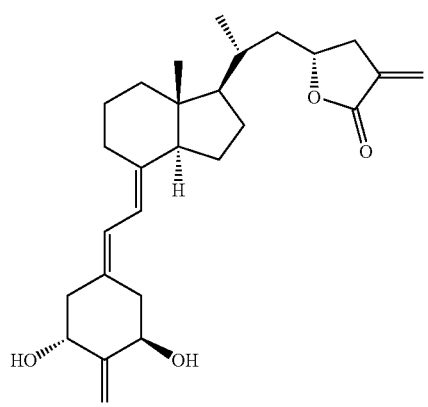

1A2

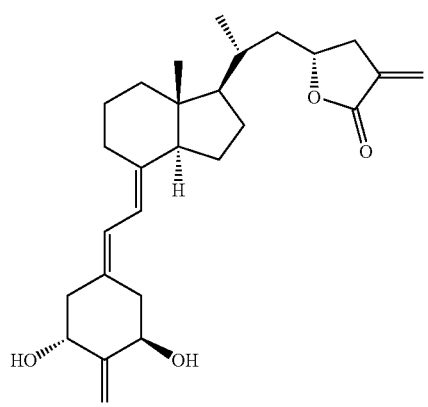

1B2

14. The method of claim 10, wherein the animal subject is human.

* * * * *